US007917211B2

(12) United States Patent
Zacouto

(10) Patent No.: US 7,917,211 B2
(45) Date of Patent: Mar. 29, 2011

(54) INOTROPIC ORTHORHYTHMIC CARDIAC STIMULATOR

(75) Inventor: Fred Zacouto, Paris (FR)

(73) Assignee: Medtronic Inc., Minneapolis, MN (US)

( * ) Notice: Subject to any disclaimer, the term of this patent is extended or adjusted under 35 U.S.C. 154(b) by 1364 days.

(21) Appl. No.: 11/381,690

(22) Filed: May 4, 2006

(65) Prior Publication Data

US 2006/0247701 A1    Nov. 2, 2006

(30) Foreign Application Priority Data

Nov. 6, 2003  (FR) ..................... 03 13055
Feb. 20, 2004 (FR) ..................... 04 01736
Oct. 27, 2004 (WO) ............ PCT/FR2004/002767

(51) Int. Cl.
*A61N 1/362* (2006.01)
(52) U.S. Cl. ............................................. 607/9
(58) Field of Classification Search ............. 607/14, 607/9
See application file for complete search history.

(56) References Cited

U.S. PATENT DOCUMENTS

| 3,857,399 | A | 12/1974 | Zacouto |
| 3,939,844 | A | 2/1976 | Pequignot |
| 4,052,911 | A | 10/1977 | Feldstein |
| 4,280,502 | A | 7/1981 | Baker |
| 5,213,098 | A | 5/1993 | Bennett |
| 5,305,745 | A | 4/1994 | Zacouto |
| 5,306,293 | A | 4/1994 | Zacouto |
| 2003/0074029 | A1 | 4/2003 | Deno |

FOREIGN PATENT DOCUMENTS

| FR | 1237702 | 6/1960 |
| WO | WO 02/53026 | 7/2002 |
| WO | WO 03/020364 | 3/2003 |

OTHER PUBLICATIONS

PCT International Search Report as issued in International Application No. FR2004/002767 mailed Jun. 17, 2005.
Wayne Cooper, Circulation, vol. 88, No. 6, 2962, Dec. 1993.
F. Zacouto, LaNouvelle Pressue Nedicale, 1974, vol. 3, No. 22, p. 1448.
Dtsch. Gesellsch. Kreislauff, 29 Congress, pp. 255-261, 1963, Steinkopff Verlag Darmstadt.
K. Theissen et al., Klin. Wschr. 52, 1082-1084, 1974, Springer-Verlag.
Roy et al., Nat. Biotechnol. Mar. 22, 2004(3):297-305 (Epub. Feb. 15, 2004) (Abstract Only).
N. Mirochnik et al., Arch. Mal. Coeur, Paris, 93, 10 Cot. 2000 (Abstract Only).

*Primary Examiner* — Carl H Layno
*Assistant Examiner* — Brian T Gedeon
(74) *Attorney, Agent, or Firm* — Campbell Nelson Whipps LLC

(57) ABSTRACT

Programmable and implantable automatic heart stimulation device (OIST) for controlling the heart, accompanied by a marked increase in the contractility of the myocardial cells on each beat produced by an optimized post-extrasystolic potentiation effect. The OIST does not cause lasting fatigue of the myocardium, markedly increases the coronary rate instantaneously and durably, causes dilatation of the walls to regress and opposes thromboses and arrhythmia. The OIST creates a genetic involution of the pathological process either by the mere effect of the mechanosensitivity of specific genetic expressions or by the addition of partial autologous cell dedifferentiation, obtained by original genetic manipulation which induces physiological an anatomical regeneration. This method also allows physiological auto-contractile living arterial stents, in particular coronary stents to be created, as well as the grafting of dedifferentiated myocardial cells.

7 Claims, 11 Drawing Sheets

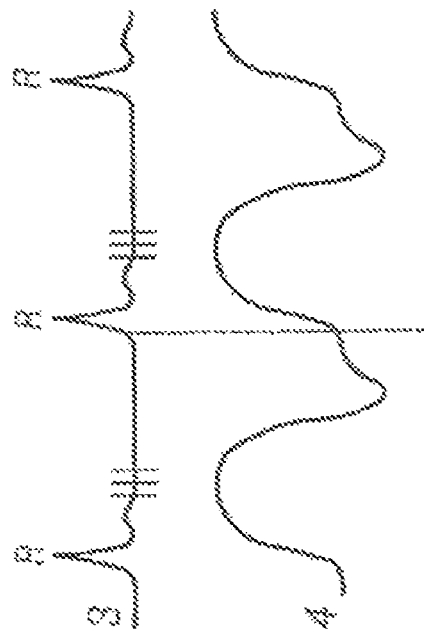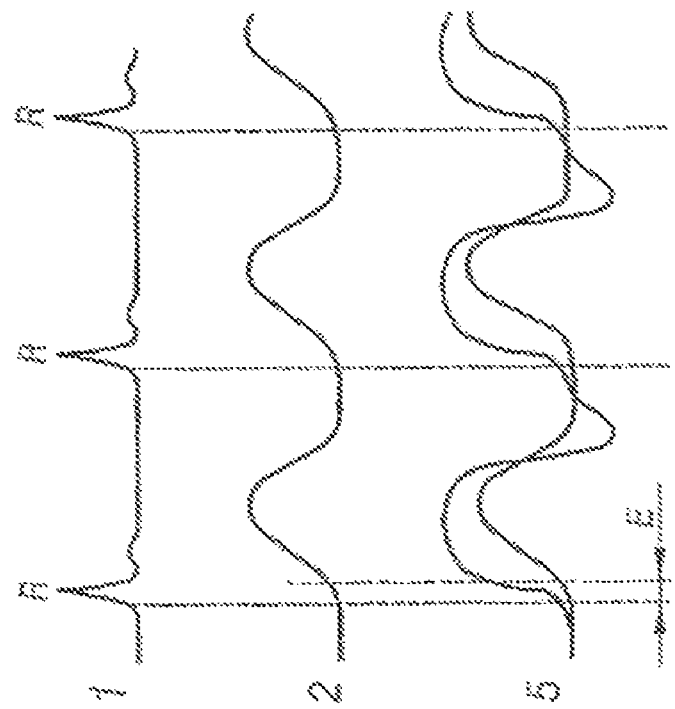
FIG. 10

INOTROPIC ORTHORHYTHMIC CARDIAC STIMULATOR

CROSS REFERENCE TO RELATED APPLICATIONS

This patent disclosure claims priority to and all benefit from international application number PCT FR 2004/002767 and French national applications; namely serial number 0313055 filed Nov. 6, 2003 and serial number 0401736 filed Feb. 20, 2004, the contents of the foregoing are hereby fully incorporated herein by reference in their respective entirety.

The invention relates to a device for electrical stimulation of the heart for, in particular, improving hemodynamic performance, performance of the heart cells and, in particular, blood flow, in particular in patients suffering from heart failure or from tachycardia or arrhythmia, and in particular from left or right, systolic, diastolic or global, severe or acute heart failure.

The invention also relates to a process for controlling such a device.

The invention further relates to a process for electrical stimulation of the heart and for heart cell improvement using such a device, in particular in patients suffering from heart failure or tachycardia or arrhythmia and in particular from acute, left, right or global cardiac failure.

Up until now, automatic heart stimulating devices, also known as pacemakers, were basically intended to replace or regulate the spontaneous electrogenesis of heart muscle activation.

A significant step has been taken in the control and reduction of isolated tachycardia, tachyarrhythmia or extrasystoles in the process and devices described in the Zacouto patents U.S. Pat. No. 4,052,991 and U.S. Pat. No. 3,857,399. These improvements enabled the coupling intervals of electrical stimulation, in particular, to be modified as a function of the variable duration of the previous cycle or cycles, for example as a percentage of this duration. These improvements also allowed the stimulations to be transmitted in a burst and in gradients. They also allowed differential marking of the spots of local detection and stimulation on the electrocardiogram.

Paired stimulation (PST) or coupled stimulation (CST) and optimum inotropic stimulation (OIST) attempts to induce, manually or automatically, a periodic succession of myocardial inhibition and stimulation preferably with parameters for obtaining maximum hemodynamics and anti-rhythmic protection. The OIST basically allows greater mobilization of the reserves and acquisitions of energy from the myocardium which are generally greater, the more fatigued the myocardium (Wayne Cooper: Postextrasystolic Potentialisation, Circulation, vol. 88, no. 6, 2962, Dec. 1993) such as, for example, increased activation of a pentose cycle in addition to the Krebs cycle (hexoses) and/or potentiated and resynchronized activation of specific ion channels and transmembrane electrons, the increase in intracellular concentrations and liberations of calcium ions, secretions of vaso-active or myoactive peptides and changes of specific local genetic expressions, translations and transductions of adaptations to potentiated biochemical myocardial energy of the "sporting heart" type. This instantaneous, significant and lasting potentiation, without a known limit over time, in contractility after specific extrasystoles is well known to cardiologists under the name of post-extrasystolic potentiation (PESP). PESP is a frequent natural phenomenon which demonstrates the possibility of further mobilizing the acquisition and the expenditure of myocardial energy reserves which often remain inhibited during failures thereof (apart from specific ectopic tachycardia). The continuation of the PESP, even in the case of acute grave failure of the myocardium (example: pulmonary edema after recent previous extended infarction of the myocardium) or chronic myocardium failure (Classificat. New-York Heart Assoc., classes 2 to 4) shows the possibility of using PST in these clinical cases.

However, paired stimulation (PST), which has been known, in particular, since 1964 and widely tested in animals and in several clinical trials to reduce or better withstand specific tachycardia and myocardial failures (for example: F. Zacouto et coil., Paris, Nouv. Presse Med. 1974, 3, No. 22, p. 1448), is still virtually never used in cardiology. This is due to the use of heart stimulation and detection equipment which is tragically inadequate as it is incapable of continuously targeting the narrow critical zones and is often unstable in each cardiac cycle (CC) which it is however essential to reach in order to carry out optimum continuous effective PST which is economical in oxygen and anti-arrhythmic.

In general, currently used devices do not allow the hemodynamic performance of the heart muscle to be durably improved by electrical stimulation, particularly in the case of patients in whom this performance is significantly reduced, in particular in those with grave heart failure.

The phenomenon of post-extrasystolic potentiation (PESP) has been observed since the 19th century.

Thus, the applicant was able to obtain a temporary improvement in hemodynamics in two patients suffering from acute left ventricular failure, by coupling, after initial manual adjustment, a paired stimulation comprising bursts of successive stimulating pulses which are brought together in the same coupled cardiac cycle on the wave R toward the end of the refractory zone (F. Zacouto et al., Paris, Nouv. Presse Med. 1974, 3, No. 22, p. 1448).

Considerable research was then carried out into the phenomenon of post-extrasystolic potentiation in an attempt to benefit from the improvement in the mechanical contraction triggered by the transmission of electrical stimulations inducing a stimulated extrasystole (see, for example, the documents U.S. Pat. No. 3,939,844 and U.S. Pat. No. 5,213,098). Despite considerable work over a long period, however, the researchers finally came to the conclusion that the problem of establishing, in a durable and effective manner, myocardial contractility potentiation by paired stimulation could not be solved and, even though this principle looked promising, the results of the trials were discouraging (see, for example, N. Wayne Cooper: Postextrasystolic Potentialisation, Circulation, vol. 88, no. 6, 2962, Dec. 1993).

These failures can be explained, in particular, by the fact that the electrical refractory functional zones (ERZ) and myocardial refractory functional zones (MRZ) and the corresponding metabolic reactions can vary significantly during each cycle, in particular in the case of myocardium suffering or of irregular rhythm disorders.

More recently, suggestions have been made regarding the creation of apparatus capable of sending to the heart paired or coupled bursts of pulses intended either to induce a sensitization action on the myocardium during the electrical refractory period, according to a hypothesis, or to generate, just after the end of the electrical refractory period, an electrosystole intended to induce post-extrasystolic potentiation during a subsequent systole. Various documents deal with research into potentiation, such as WO 02/53206 and WO 03/20364.

It was found during this research, however, that paired or coupled stimulation is not compatible with arrhythmia or tachyarrhythmia, which is common, in particular, in patients suffering from cardiac failure, when it does not induce them itself in hearts that are already unstable.

Faced with problems and discouraging conclusions from the research, the present invention proposes to provide a device and processes for durably and significantly improving the hemodynamic performance of the heart by electrical stimulation.

A further object of the invention is to treat arrhythmia or tachycardia, even tachycardia which are recurrent or cannot quickly be reduced by anti-tachycardic pacemakers (Zacouto, U.S. Pat. No. 3,857,399 and U.S. Pat. No. 4,052,991), even in patients suffering from cardiac failure, and to instantaneously improve hemodynamics, whether or not the tachycardia is reduced.

In its general scope, the invention proposes to improve a heart muscle stimulating device allowing a significant increase in the hemodynamic performance of the heart and/or the treatment of tachycardia comprising a device which is preferably implanted permanently and comprises:

means for automatic acquisition of the heart rhythm, for detecting, in particular, the interval between at least the last two waves R (induced or spontaneous) of the cardiac cycle just completed, means for determining, preferably in real time, the duration of the electrical refractory period (ERZ) following the last wave R of said cycle, and means for sending at least one stimulating pulse, substantially without delay toward or at the end of said refractory period (ERZ).

The coupling stimulating pulse or that pulse of the burst which stimulates the heart generates a wave (R') which does not cause a mechanical reaction but induces an additional electrical refractory zone (RZ) contributing to the desired inotropic and anti-arrhythmic effect.

The invention relates to a device for stimulating and/or potentiating the heart muscle and/or the myocardial cells, allowing a significant increase in the hemodynamic performance of the heart and/or the treatment of tachycardia, tachyarrhythmia or auricular fibrillation, comprising:

means for the automatic acquisition of the heart rhythm and, optionally of its origin, for detecting, in particular, the interval between at least the last two waves R (induced or spontaneous) of the cardiac cycle just completed, means for the precise acquisition of the cardiac hemodynamics, means for determining, continually in real time, the duration of the electrical refractory period (ERZ) following the last wave R of said cycle, means for evaluating at least one parameter relating to the functional cell state of the myocardium, and means which are subordinate to said evaluating means for sending at least one paired or coupled stimulating pulse adapted to said functional cell state substantially without delay at the end of said refractory period (ERZ).

In a particularly preferred manner, said evaluation means determine an effective critical zone (ECZ) to target, which is placed immediately after the end of the electrical refractory zone and terminates at the end of a maximum myocardial contraction refractory zone (MMRZ), the transmission of said stimulating pulse occurring in said zone (ECZ), if it is present and targetable and does not induce untreatable arrhythmia. In the latter case, means for automatically retarding the zone ECZ, for example by 20 ms to 20 ms, are provided, while the hemodynamics and metabolic consumption of the myocardium are monitored.

Preferably, said evaluation means attempt to detect or check the myocardium excitability threshold during each cycle.

Preferably, according to the invention, the device is arranged so as to determine the duration of said electrical refractory period (ERZ) during each cycle and preferably in real time.

Advantageously, the refractory zone is determined in a part of the heart into which the stimulating pulse or burst is sent, for example by using the same electrodes for detection and stimulation, or very close electrodes.

In an advantageous embodiment, the means send, substantially at the end of said refractory period (ERZ), a burst of stimulating pulses, the duration of the burst and the pulses repetition interval being such that a stimulating pulse of the burst is sent to the heart substantially without delay after the end of said refractory period.

Preferably, the stimulating pulse sent toward or at the end of the refractory period is sent, almost without delay, for example between 10 and 20 ms after the end of the refractory zone ERZ. In the case of a burst, however, it is necessary for the beginning of the burst to be produced within and toward the end of the refractory period.

It is found that the contractility and hemodynamics generated by at least one of the stimulating pulses of the burst can be potentiated by a mere implanted device, in particular in the case of acute or severe cardiac failure.

At the same time, a significant permanent reduction of the ventricular rhythm and potentiation of heart contractility are obtained in tachycardic hearts.

As a particular result, significantly more powerful cardiac contractions are obtained but do not lead to an unacceptable over-consumption of oxygen by the heart, because the increase in oxygen consumption is compensated by the concomitant increase in the coronary flows and over-compensated by the gain in contractility.

The device is thus capable of carrying out optimum inotropic paired or coupled stimulation, hereinafter called OIST.

The duration of the refractory zone ERZ of the current cycle can be determined from characteristics of the preceding cycle or even from earlier cycles. For example it can be evaluated a priori as a percentage of the earlier cycle duration, which percentage increases if the duration of the cycle is decreasing. For example, the percentage will be from 25 to 30% in the case of a rhythm of 60 p/mn and from 50 to 80% in the case of a rhythm of 120 p/mn.

The duration of the refractory zone can be evaluated by any other means already known to cardiologists, for example by progressive scanning of an electrical pulse in a burst which is retarted from cycle to cycle until a generated electrosystole is acquired. The duration ERZ obtained can thus be used during one or more following cycles to transmit the stimulating pulse or burst of pulses.

If the device generates a single stimulating pulse instead of a burst, the means (4) for determining the duration of the refractory zone are arranged so as to acquire, by scanning a second pulse, the substantially exact duration of the refractory zone, this scanning being carried out, for example, during the preceding or current cardiac cycles.

If a burst of stimulating pulses is used, it will preferably begin just before the estimated end of the refractory period ERZ, and the duration of this burst and consequently the number of stimulating pulses will advantageously be such that a stimulating pulse can occur very quickly after the end of said refractory period.

These means for determining the duration of a refractory zone of the heart are known to cardiologists.

In a variation of the invention, if the stimulation at the end of the refractory period ERZ is carried out by transmission of a burst of pulses, the device can transmit the burst substantially before the estimated end of the refractory period ERZ and detect without delay in the same cycle, preferably at the same location of the heart, which of the pulses of the burst induces an electrosystole R' for a given stimulation amplitude, and this provides the duration ERZ which has just elapsed. This detected duration also enables the likely duration of the refractory zone ERZ of the following cycle to be determined.

Preferably there are provided anti-tachycardic stimulation means and extrasystole-sensitive means for automatically stopping said stimulation if excessive hemodynamic instability or electrical arrhythmia corresponding to predetermined criteria occur.

In a developed embodiment, the determination of the refractory zone ERZ of the cycle to come can be refined by allowing for one or more detected parameters while allowing for the functional and rhythmic stability of the heart.

These parameters can be, in particular:
duration of the earlier or current cycle or cycles, hemodynamic parameters, metabolic consumption and excitability threshold over a specific number of comparable successive contractions, by comparison with thresholds.

In the event of significant discordance between, for example, the zone ERZ calculated using the ratios between the intervals QT and the actual intervals RR of the patient, as known in cardiology, and the measured zone ERZ, the myocardium can undergo a metabolic change which can precede either a grave arrhythmia if the ERZ is decreasing or re-establishment of function if the ERZ is increasing.

The apparatus monitors and distinguishes between these two cases and reacts instantaneously according to programming. In the case of grave arrhythmia, for example, stimulation is stopped or the stimulation parameters are modified.

The burst of stimulating pulses may be advanced or retarded relative to an estimate of the refractory zone and/or the pulse interval in the burst and/or the reduced or increased pulse amplitude, the device having automatic acquisition means, in particular by obtaining the intracardiac ECG for determining which stimulating pulse in the burst triggered the wave R' and consequently by possibly modifying the burst.

A device of this type will be particularly indicated for reduction of tachycardia, including sinusoidal tachycardia, in patients suffering from cardiac failure.

Preferably, the device comprises means which are sensitive to spontaneous or stimulated waves R and/or to the determination of the electrical and mechanical refractory zones, in particular by scanning all of the burst or only within this burst and/or means for the determination without delay of the heart excitability thresholds, for example by providing stimulating pulses of variable intensity, including subliminal pulses for allowing the measurement thereof. It is also proposed to be able to control the stimulator as a conventional anti-tachycardic auto-rhythmic stimulator reacting to the extrasystoles and to be able to automatically stop the programmed OIST on occurrence of excessive hemodynamic instability. In the event of excessive instability of the refractory zones or myocardium excitability thresholds or the two simultaneously, the durations and/or the number and/or the voltage of the pulses of the bursts can, for example, be increased or the stoppage of operation from a threshold can be programmed.

Preferably, the device is characterized in that it further comprises means for very precise acquisition of the cardiac hemodynamics.

These means are known per se and preferably comprise one or more intracardiac pressure sensors or such sensors disposed in the vicinity. Preferably, sensors for determining variations in heart volume, for example known, in particular juxta- and intracardiac electrical impedance proximity sensors, are also used for acquiring precise pressure/volume curves of cardiac contraction.

In a perfected embodiment of the invention, a device according to the invention which is implantable or even external and non-implantable, can comprise, in addition to the rhythm acquisition means, means for determining the duration of refractory zone, and pulse or burst transmission means as described above, means sensitive to the precise acquisition of the hemodynamics for determining the variations in efficacy of the hemodynamics, these means being capable of controlling the transmission and optionally the parameters of the pulse or of the burst and/or the administration of an external perfused dose of medicament which is controlled or based on an implanted medicament reservoir until a degree of hemodynamic performance is obtained which is, for example, programmed or determined in advance, or in a manner resembling that which produced the most favorable hemodynamics for the patient at a given moment.

Various aspects of the invention will now be described.

Control of OIST

In general and particularly in the case of severe or acute failure, the present variations in the electrical refractory zones (ERZ), the mechanical refractory zones (MRZ), the excitability thresholds, the hemodynamics and the metabolic behavior cannot themselves anticipate the development of the intramyocardial functional state of the electromechanical coupling (EMC). The electromechanical coupling (EMC) can be observed only by precise, individualized specific temporal comparisons that can be provided by the device according to the invention, in particular in the form of an analyzing simulator (ASIM), without which rapid myocardial failures can remain unpredictable and unstoppable by OIST.

Continuous Optimum Maintenance of OIST Parameters Relative to Variations in the Myocardial Excitability Thresholds In a preferred embodiment of the invention, the excitability threshold of the heart is monitored continuously by means of a periodic reduction in the stimulating energy used according to the Zacouto patent FR-A1-1,237,702, PV 651.632 of Jul. 11, 1953 and allowing an instantaneous readjustment of the stimulating parameters. One method of achieving this can consist in progressively or abruptly reducing the stimulating pulse of the pulse train until this pulse is recaptured. During the periods when this pulse remains ineffective, the following pulse in its train takes control of the heart. If a reduction in stimulating energy remains sufficiently reliable, the OIST can be programmed to trigger a stimulation, for example of reduced amplitude, and this also reduces the risk of inducing extrasystoles. The amplitude close to the threshold of the first three of four pulses in a train comprising six or eight pulses can also be reduced, for example, by one third, in order to observe whether or not this targeted subliminal stimulation promotes the myocardial excitability threshold. If this threshold turns out to be reduced, this "facilitation" can be quantified, for example, as a percentage of reducible amplitude, and its duration of facilitation can be measured by a periodic repetition of this examination.

Conversely, a disruption in the stimulating pulse or the complete stimulating train will trigger an instantaneous increase in the energy amplitude of the pulse which has become subliminal or of the entire stimulating train of the next cardiac cycle. In the case of the following cardiac cycles, a pulse gradient with a progressively increasing voltage can advantageously be used for determining, by automatic measurement within each cardiac cycle, for the inotropic orthorhythmic software program, the new myocardial excitability threshold from which a new process for control and intervention in the stimulating pulse amplitude will be triggered.

Thus, the OIST performs optimum continuous instantaneous adaptation of the stimulating intensities according to their coupling intervals relative to the preceding wave R, whether it is a spontaneous reduction or increase in the myocardial excitability thresholds.

When attempting to specify a myocardial excitability threshold, it is observed that it is not a spot limit but a zone between the subliminal amplitude where there is no propagated stimulation and the supraliminal amplitude where a constant propagated drive element is observed. The extent of this inconstant excitability zone is variable.

In a particularly preferred manner, the device comprises means for giving a pulse intended for electrical stimulation an amplitude greater than at least 30% and preferably between 30% and 90% of the amplitude of the last subliminal pulse observed.

The parameters on which the device acts can be merely a programmed ventricular rhythm and/or an automatic adjustment of the beginning or the end or the duration of the burst or the number or the characteristics (in particular width, polarity, intensity) of the pulses in the burst, or else a location of the transmission of the burst over various stimulating electrodes. For example, a burst can be reduced progressively to a single pulse. For this purpose, it is possible to probe periodically with at least a second pulse which moves progressively from, for example, 25 ms ahead of the stimulating pulse and then retracts step by step, for example by 4 m/s during each cycle so as to automatically measure the beginning of the non-refractory zone. When the exploratory pulse retracts toward the stimulating pulse, this pulse itself is retracted until the beginning of the reduction in the ventricular pressure/volume curve or the increase in the oxygen consumption and/or the membrane secretion and accumulation of electrons or, for example, proximal catecholamines or lactic acid are obtained, this position corresponding to the exceeding of the end of the mechanical refractory zone with maximum active contraction known as MMRZ.

There are preferably provided means for anti-tachycardic stimulation and means sensitive to the extrasystoles for automatically stopping said stimulation if excessively great hemodynamic instability or electrical arrhythmia corresponding to predetermined criteria occurs.

The electrical stimulation of the heart according to the invention allows the obtaining, during each cardiac cycle (CC), of an optimum inotropic stimulation (OIST) which is paired (PST) or coupled (CST) by very precise adjustments of the pulses relative to the electrical refractory functional zones (ERZ) and myocardial refractory functional zones (MRZ) and to the corresponding metabolic reactions and in space relative to the cardiac locations of the electrodes, allowing the best hemodynamics or anti-arrhythmic efficacy to be obtained.

These functional zones can vary significantly during each cycle, in particular in the case of myocardial disorders. In order to control the ERZ and MRZ and the corresponding hemodynamics during each cycle, these zones can be analyzed continuously and in real time, for example using the means described in the Zacouto patents, U.S. Pat. Nos. 4,052,991 and 3,857,399.

The device can comprise means for progressively reducing a burst to a single pulse or a small number of pulses, in particular by periodically probing with at least a second pulse which moves progressively ahead of the stimulating pulse to automatically measure the beginning of the non-refractory zone so that, when the exploratory pulse retracts towards the stimulating pulse, the stimulating pulse can be retarded, in particular periodically in the event of instability in operation until the beginning of the reduction of the ventricular pressure/volume curve or increase in the oxygen consumption and/or a corresponding parameter, in particular the membrane secretion of electrons, local pH or ketone bodies is obtained, this position corresponding to the exceeding of the end of the mechanical refractory zone with maximum contraction (MMRZ).

It can comprise means for passing from paired stimulation to coupled stimulation, in other words to a completely stimulated rhythm, said means being sensitive to the means for acquisition of the electrocardiogram and/or of the hemodynamics and/or of the myocardial metabolism.

Instantaneous Inhibition of Extrasystoles or Arrhythmias During OIST

The device according to the invention can also be arranged to treat extrasystoles and arrhythmias which can appear either spontaneously or due to the operation of the device.

Perfect operation of the OIST entails instantaneously detecting the premature extrasystoles which can follow or accompany a pulse train and also reacting instantaneously by inducing a stimulation or a stimulation train from the beginning of detection of such an extrasystole. The instantaneous detection of a premature extrasystole necessitates an ECG recording that is preferably independent of its intramyocardial directional propagation, which is slow (1 m/sec), before arriving at the intracardiac detecting electrode. Detection by juxta- or extra-cardiac or ventricular intracavitary electrodes, preferably without contact with the myocardium, which are sensitive to the speed of propagation of the variations in the electrical field of the heart, which is close to the speed of light, can be used for this purpose.

Once the detection of a premature extrasystole has been confirmed, the anti-arrhythmic program will instantaneously trigger a stimulation, preferably in a burst, from all the stimulating electrodes available in order to induce as soon as possible a fusion complex between the propagations of the stimulated and extrasystolic depolarizations. This fusion complex will block the propagation of extrasystolic depolarization and frequently allow the suppression of premature myocardial ectopies. If premature myocardial ectopies, in particular those which are repeated, threaten the efficacy of the OIST, the diastoles can be instantaneously and temporarily shrunk in order to close the non-refractory intervals of the cardiac cycles during which the triggering of the premature extrasystoles can occur.

In an embodiment of this type for the treatment of isolated arrhythmias and extrasystoles, the device according to the invention can comprise a plurality of electrodes disposed at different locations of the heart muscle and/or at a distance from the heart and acquisition means which are sensitive to the electrical signals appearing at the electrodes and remotely from them for observing, at an early stage, the occurrence of an electrical extrasystole in a myocardial zone close to those of the electrodes initially concerned. The stimulating pulse sending means are thus made sensitive to such an observation so as to emit instantaneously, in a nearby electrode or in a plurality of electrodes, a stimulating pulse or burst of which the electrical propagation into the myocardium is directed toward the myocardial zone affected by the extrasystole and causing fusion between the spontaneous and stimulated depolarizations which blocks the propagation of the extrasystole.

In order to be able to detect sufficiently early and, in particular, to be able to immediately send a stimulating pulse into the vicinity of the territory currently affected by extrasystolic depolarization, the device is preferably connected to a plurality of electrodes such as electrodes in the region of the coronary sinus, electrodes of the septum and the free ventricle walls and preferably juxta-cardiac, extra-cardiac or intracavitary electrodes, the device being arranged so that the acquisition means detect the electrode close to the origin of the extrasystole, the means for transmitting a stimulating pulse or a burst being arranged so as to send the stimulation at least from an electrode remote from the origin of the extrasystole.

Therefore, when the OIST is disturbed by untimely occurrences of extrasystoles which are apparently self-induced, the suppression thereof is promoted by an instantaneous electrical response capable of occupying, at the earliest stage, the still non-refractory zones of the myocardium. For this purpose, it is preferable to detect the extrasystoles, not in the region of bipolar intracardial catheters but in the extracardial region. In fact, intracardial detection only "sees" the extrasystole coming with a delay corresponding to its speed of propagation from its creation until the arrival below the detecting electrode which takes place at an intramyocardial speed of approximately 1 m/second. On the other hand, an electrode which is more external to the heart "sees" the myocardial depolarization propagating at a speed close to the speed of light. The extrasystoles, in particular those considered dangerous by the programming, should therefore be detected by means of juxta- or extra-cardial electrodes; as soon as such a detection which is confirmed to be critical appears, a burst of stimulations should be induced in the region of one or more or preferably all of the stimulating electrodes. If there are a plurality of stimulating electrodes, stimulation should be carried out simultaneously from them so as to induce fused QRS complexes which block the non-refractory myocardial spaces and thus prevent propagation of new extrasystoles. This system should preferably act within a single mechanical cardiac cycle.

The sequential recording of extrasystolic events, in particular dangerous extrasystolic events, allows registers to be created according to Zacouto's U.S. Pat. No. 5,306,293; this opens up the possibility, in the event of crisis repetition, of carrying out preventive stimulation, in particular temporary acceleration of the basic rhythm before the reoccurrence of these extrasystoles.

In a further embodiment, wherein the device comprises means for rapidly detecting an extrasystole, the means of the device are sensitive to the acquisition of this extrasystole for reducing or even suppressing, preferably temporarily, the electrical diastolic phases (D). This is effected either by increasing the stimulation rhythm in a heart under electrical control of the device or by taking the control to send a stimulating pulse at the very beginning of the electrical diastole.

In these latter cases, the device according to the invention passes from the state of paired stimulation to the state of coupled stimulation.

The installation of tachycardia can thus be prevented while maintaining a rhythm well below the first tachycardiac rhythm and while benefiting from a post-extrasystolic potentiation effect.

A device of this type is particularly effective in controlling nascent arrhythmias induced by stimulation or originating close to the zone or zones into which the stimulating pulses or bursts are sent.

In a further embodiment, the number and/or intensity of pulses of the burst can be temporarily increased on appearance of an arrhythmia in order to potentiate the effect of stabilization on the myocardial cell membranes or automatically administer, by an OIST program, a drug which perfuses or comes from an implanted medicament reservoir (see, in particular, Zacouto, U.S. Pat. No. 5,305,745).

In other cases, the device can be arranged so as, on the other hand, to reduce the intensity of the pulses of the burst in the event of arrhythmia, the device then monitoring whether arrhythmia continues. In this case, the intensity of stimulation could be increased.

In a further embodiment, the device according to the invention can be effectively used in the event of auricular fibrillation, leading to ventricular arrhythmia. The device according to the invention is arranged so as to acquire the cardiac mechanogram, preferably until the occurrence of a cycle which is sufficiently long to obtain a good myocardial contraction relative to the current instantaneous rhythm defined, for example, by a preprogrammed threshold and the stimulating means then transmit a stimulating pulse or burst at an instant within the systolic plateau of the mechanogram curve, in other words from the relatively flattened peak of the mechanogram curve.

Once the device has acquired an immediately preceding cycle, the electrical refractory period ERZ can be situated as a percentage of the duration of the preceding cycle, the pulse being launched into said plateau of the hemodynamic curve preferably just before the end of this contracted maximum mechanical refractory zone, for example 30 to 40 ms before the end of this zone MMRZ, this zone end being detectable by an intramyocardial local pressure microsensor at the point close to the active electrode for transmitting a burst of pulses spaced by 15 ms, after which the device immediately stimulates, preferably in a multipolar manner, after the end of the electrical refractory zone which has just been extended, thus canceling the electrical diastole. Advantageously, this can be carried out on electrodes located in the vicinity of the zone which saw the arrhythmia appear by using electrodes disposed in the above-described manner.

For example, the device can firstly stimulate the atrium with an intra-auricular electrode then, if necessary, the ventricle with an intra-ventricular electrode, in a succession which is well known in pacemakers of the DDD type. The auricular myocardial tissue can thus be regenerated or improved by OIST stimulation in the auricular region.

In a further embodiment, when the patient's His bundle is more or less blocked, for example by Digoxin, the frequency of stimulation can be progressively reduced while monitoring premature contractions of auricular origin.

The device according to the invention can be integrated in an automatic defibrillator (IAD), for example an implanted defibrillator, and can be used, in particular after a defibrillation shock, or else to prevent grave arrhythmias.

The implanted defibrillators currently comprise anti-tachycardic means of the anti-arrhythmic type according to Zacouto's U.S. Pat. No. 3,857,399, and the device according to the invention can, for example, be actuated when the anti-tachycardic device does not manage to rapidly reduce a tachycardia.

Inotropic Stimulation During the Muscular Refractory Zone of Maximum Contraction (MMRZ)

In a preferred method of optimization, the software controlling the device according to the invention is programmed so as to automatically find the narrow effective zone MMRZ in each cycle concerned and optionally to then reduce the various parameters of the pulse bursts, in particular the number pulse bursts, so as to end up, if possible, with a single perfectly targeted pulse. Since such stability in operation of the OIST is non-existent or inconstant, particularly in the case of myocardial suffering, the programming which continuously detects the mechanical parameters, preferably with the metabolic (oxygen or equivalent) consumption thereof, should reverse the burst reduction process (in the event of adequate or increasing instability), so as to find the location of the new useful narrow zone of the cycle without delay with the bursts. A fast method for finding the zone MMRZ involves detecting, within a burst, the effective pulse which produces propagated depolarization and progressively reducing its distance from the preceding pulse until it is disrupted and no longer leads to visible electrogenesis on the electrocardiogram which will be induced, at this moment, by the following pulse of the burst. The beginning of the useful zone is thus known precisely and it is possible to add approximately 20 ms and to consider that this interval represents the useful zone at a given period. This automatic research, which is harmless to the patient, should be repeated periodically so as not to lose the exact location of the MMRZ during the variations thereof. After the effective pulse of the pulse burst has been found, the voltage or the width of the other pulses can be reduced so as to render them slightly subliminal, and this can maintain their anti-arrhythmic effect as a functional sentinel, because a subliminal pulse close to the threshold often influences this threshold by reducing it for a short period (facilitation effect). This phenomenon can be measured automatically while slightly reducing the intensity of the pulse or pulses preceding the stimulating pulse in a burst and while progressively reducing the intensity, the voltage or the width of the stimulating pulse until its functional disruption, the following pulse of the burst maintaining a stimulating intensity; the intensity of this pulse can then also be reduced progressively so that the variation in its excitability threshold can be measured and, by shifting it progressively over time, the duration and intensity of this facilitation effect can thus be measured.

In a variation, for detecting the maximum contraction zone MMRZ, the device can comprise means for the precise measurement of the volume of the heart or of a part of the heart by electrical impedance or else by localized echography, for example in that it comprises a tissue-measuring echographic ultrasonic probe which is oriented toward a heart wall in order to measure the displacement thereof, thus allowing the variations of the myocardial volume to be obtained in real time and the moment of the maximum contraction thus to be determined.

The invention accordingly relates to a device for stimulating and/or potentiating the heart muscle and/or the myocardial cells, for significantly increasing the hemodynamic performance of the heart and/or the treatment of auricular tachycardia, tachyarrhythmia or fibrillation comprising:
means for the precise acquisition of the cardiac hemodynamics (5, 6) and comprising a means for instantaneous detection of the maximum myocardial refractory zone (MMRZ) at a precise location of the myocardium,
and means for sending at least one stimulating pulse and preferably a burst of stimulating pulses from the local region in which the occurrence of the zone MMRZ is detected.

It preferably comprises means for automatic acquisition (1, 2, 3) of the heart rhythm and optionally of its origin, in particular for obtaining the interval between at least the last two waves R (induced or spontaneous) of the cardiac cycle which has just been completed and means (4) for determining continually in real time the duration of the electrical refractory period (ERZ) following the last wave R of a cardiac cycle, said device being arranged so as to detect whether an electrical depolarization signal has been produced by said stimulation in said zone MMRZ.

These means allow the detection and storage of the duration of said maximum myocardial refractory zone (MMRZ) and the sending of said local stimulating pulse or burst of stimulating pulses after a short duration after the beginning, in the current cycle, of the beginning of said zone MMRZ and before the estimated end of said zone by storing said duration in the preceding cycles.

According to the invention, the stimulating pulse or at least one stimulating pulse of a burst falls in said zone (MMRZ), substantially at the location of the myocardium where the occurrence of said zone (MMRZ) is detected.

The device can comprise implanted means for measuring intracavitary pressure and capable of detecting a zone of maximum pressure in the plateau of the cardiac mechanogram and to which said means of transmitting a stimulating pulse or burst are sensitive.

Preferably, it comprises at least one sensor for detecting intramyocardial pressure. Said intramyocardial pressure sensor is situated in the intra-auricular septum and/or in a free cardiac or intra-ventricular wall.

In a variation there can be provided means for measuring the variation in the volume of the heart or a part of the heart, detecting and storing the interval of the cycle where said volume has reached and maintained its minimum value, said means for sending a stimulating pulse or burst being sensitive to said measuring means.

There can thus be provided means for detecting the oxygen consumption of the heart and/or an equivalent, in particular the local pH or concentration of ketone bodies, and means for detecting the zone of maximum cardiac contraction (MMRZ) by estimation by detecting, during one or more previous cycles, the relative position in the cycle and/or in the mechanogram of the pulse or of the pulse of a burst which has generated post-extrasystolic potentiation (PESP) with minimal oxygen consumption relative to the measured blood flow per minute.

Comparative Analysis with Simulation

A safety OIST at clinical level necessitates effective methods of protection against interfering extrasystoles and spontaneous variations in the refractory zones of the myocardium which can be increased by the actual stimulation in bursts.

The size and speed of the variations in the electrical and mechanical refractory zones of the heart can be explained by the additional energetical force which the OIST demands during each myocardial contraction. The organism tends to avoid this force, which is imposed by very precise targeting of the pulses in each cardiac cycle, by modifying both the durations and the excitability thresholds of these zones. However, mere adaptation, even if perfect, to the various myocardial parameters is not always sufficient to detect the blood flow of each contraction, because the variations in the intrinsic parameters (intracellular electromechanical coupling) of the contractile apparatus remain unknown. It follows that precise, constant and comparative analysis by a "simulator" of the actual blood flow, in real time, relative to the preceding cycles with monitoring and possibility of automatic intervention in the OIST remains necessary.

It should be borne in mind that, in the event of grave or acute cardiac failure, the continuous maintenance of an OIST becomes more difficult, and it should be possible to anticipate the development, particularly in the short term, of the critical cardiac parameters. For this purpose, the variations in parameters which previously induced an unjustified risk of disruption of the OIST are stored and stimulation is carried out in an attempt to avoid similar concordances; in the event of justified disruption, for example arrhythmia or critical, purely myocardial failure, the OIST will be programmed to stop instantaneously with emission of an alarm and analysis of the responsible cardiac parameters and, if necessary, defibrillation or anti-tachycardic stimulation or automatic injection of drugs. These safety functions can be performed by an analyzing simulator (ASIM) employing, in particular, the comparative analysis between, on the one hand, the simulated ECG and hemodynamic and/or metabolic curves relative to patient data and, on the other hand, actual curves recorded in real time and superimposed.

The invention of the OIST, by adapting without delay to these different variations in spontaneous functional spacing of the heart, provides continuity of its optimum inotropic effect.

Analysis by theoretical simulation adapted to each patient and its difference from the actual curve of the cardiac and vascular parameters in real and deferred time allows the functional reactivity of the myocardium toward its stimulation by the inotropic orthorhythmic pacemaker to be shown continually. This OIST stimulation allows the differences between the desired curves and the actual curves as well as the variations thereof to be displayed instantaneously and magnified as desired, and this in turn allows the electrical stimulation parameters to be readjusted, if necessary, instantaneously and automatically. It is thus possible to hatch, color differently and continually quantify automatically the differences in subtraction of these curves. A manual readjustment cannot be as fast and quite frequently necessitates the prior understanding of the physiopathological mechanism concerned.

In view of the available information on a patient's heart and the functioning thereof, a simulation of the effects, which are theoretically legitimately expected, can thus be established by carrying out the process according to the invention, and this simulation and the actually effected stimulation can be compared.

In this embodiment, the device comprises:
means for acquiring information relating to a patient's electrocardiogram, including the heart rhythm,
means for acquiring information relating to the patient's hemodynamic performance,
analysis means which are sensitive to said acquisition means for simulating the effect of an inotropic paired or coupled stimulation adapted to the patient's heart.

It advantageously also comprises means for automatically comparing said acquired information on the patient's hemodynamic performance with the simulated effect on said performance of inotropic paired stimulation.

Preferably, said acquisition and comparison means allow the acquisition and comparison of information cycle by cycle.

The parameters for determining the state of a patient's heart and its reactivity include its electrocardiogram in the spontaneous state or with the assistance of a pacemaker, for example an orthorhythmic pacemaker. They also include information about the hemodynamic performance of the muscle and its reactivity to electrical stimulations. The various parameters and means for acquiring them and, in particular, for cardiac efficacy, including flow, volume and pressure, oxygen consumption etc. have been defined hereinbefore and are also described in the documents incorporated by reference thereto.

Preferably, said parameters include at least one of the following parameters relating to the contraction:
gradient (dp/dt) of the phases of ascent and/or descent of the intracavitary and/or intramyocardial pressure;
duration of the systolic pressure plateau, corresponding to systolic ejection;
duration of the systole (cardiac contraction);
duration of the diastole (fast and slow active motor filling phases);
ratio between the diastole and systole durations;
quality of the diastole, in particular filling depression;

electromechanical coupling (period separating the beginning of a QRS complex from the beginning of the mechanical systole which it causes).

Preferably, the device comprises means for comparing information about the electrocardiogram and the hemodynamic performance of a simulation of inotropic paired or coupled stimulation with corresponding information acquired during an subsequent identical or similar actual inotropic stimulation.

Preferably, it comprises means for acquiring or calculating a threshold level for values of the information on the simulated hemodynamic performance adapted to the patient and, if the threshold is exceeded, causing an identical or similar inotropic paired or coupled actual stimulation.

Said means for acquiring information relating to the patient's electrocardiogram and to the patient's hemodynamic performance are arranged so as to acquire this information at different rhythms.

Preferably, the device is arranged so as to temporarily impose, on the patient's heart, rhythms which vary in increments or progressively, during which said information relating to the electrocardiogram and said information relating to the corresponding hemodynamic performance are acquired.

Preferably, said means sensitive to the acquisition means are arranged so as to simulate the effect of a plurality of inotropic paired or coupled stimulations at different heart rhythms.

Preferably, said comparison is carried out for a limited number of cycles of actual inotropic stimulation and, if the absence of a satisfactory level of hemodynamic performance is observed, the current stimulation is terminated.

Said number of cycles may be approximately 10 or less, in particular 1, 2 or 3 cycles.

Preferably, the device is arranged so as, if an adequate increase in initial hemodynamic performance is observed, to continue the inotropic stimulation and to detect and store whether the increase in initial hemodynamic performance is maintained and/or further increases progressively for a greater number of cycles.

Said greater number of cycles is preferably at least about 100 cycles.

Said means are arranged so as to include the medicinal inotropic effects likely to interfere with the effect of electrical inotropic stimulation.

The device can comprise means for emphasizing, visually and/or quantitatively by calculation, the differences between the curves for the stimulation and for the corresponding actual stimulation.

Preferably, all this information relating to the electrocardiogram, the heart rhythm and the hemodynamic or physiological characteristics is obtained and stored in the device according to the invention, whatever the patient's spontaneous or stimulated heart rhythm. In such a case, the simulation is refined by the analysis made by comparing the variations in the parameters and in particular in the above-listed parameters, at the various rhythms.

These changes in cardiac rhythm or reactivity can also be acquired by subjecting the patient to appropriate medicaments which act, for example, on the heart rhythm and/or the cardiac contraction, for example Dopamine.

Thus, for example, the electromechanical coupling and the manner in which it can vary when the rhythm varies will give a good indication of the mechanical reactivity of the heart after stimulation. The gradient of the rise in pressure (dp/dt) will give an indication of the capacity of the heart muscle to create a rise in pressure, whereas the gradient of the drop in pressure could be indicative of the compliance or elasticity of the heart muscle and therefore of its capacity to fill during the mechanical diastole, according to the rhythm.

The device according to the invention is programmed to use the information thus acquired and propose, at least for the patient's spontaneous rhythm or base rhythm, and preferably for other rhythms, an electrocardiogram and a mechanogram simulating a result of functioning with paired or coupled stimulation according to the invention.

A simulated mechanogram thus allows, in particular, the simulated cardiac output to be obtained, and this simulated rate can then be compared with the measured rate of the patient
in a spontaneous rhythm or in a simulated base rhythm if necessary, and it can be estimated whether the implementation of inotropic stimulation according to the invention would lead to a significant increase, preferably of at least 20%, in the output, leading to a significant improvement in the patient suffering from heart failure. The production of simulations at different rhythms allows cardiac outputs corresponding to these respective rhythms to be estimated and, if necessary, a particular rhythm, in particular an accelerated rhythm, to be selected for a patient suffering from cardiac failure and having a relatively low spontaneous rhythm, or a reduced rhythm for example in the case of a patient having a high spontaneous rhythm which it is hoped to reduce by the inotropic stimulation according to the invention.

The following stages of the process according to the invention therefore involve applying the selected inotropic stimulation to the patient by means of the simulation step, instantaneously acquiring the results of this stimulation and comparing these results with the theoretical simulated results.

The device is preferably programmed so as to immediately check the changes in hemodynamic performance after a very small number of cardiac cycles, for example, during one, two or three mechanical cycles or during one or a few tens of cycles. If a significant improvement fails to appear or to be maintained, for example after three cycles, the device stops inotropic stimulation or, depending on the programming provided, attempts inotropic stimulation under different conditions, for example at a different rhythm.

If an initial actual improvement in hemodynamic performance is observed after this small number of cycles, the inotropic stimulation according to the invention is continued for at least about one hundred or a few hundred cycles, and the device checks whether the increase in initial hemodynamic performance occurring at the very beginning of inotropic stimulation is not only continuous but also progressively increases during this greater number of cycles and will be stored.

The comparison between the simulated increase in hemodynamic performance and the actual increase or change in hemodynamic performance can be obtained, for example, by superimposing the simulated and actual hemodynamic curves and measuring the differences, namely at least the difference in flow, and preferably differences from other parameters, in particular specific parameters or all of the parameters listed above.

It could be decided, for example, if the difference, in particular with regard to flow, is negative and is below a threshold, for example 10 or 20% below the simulated flow value, that the inotropic stimulation which has been carried out is not sufficient, the device thus stopping isotropic stimulation or attempting other inotropic stimulation.

On the other hand, if the increase in hemodynamic performance exceeds the simulated increase by a value, for example, of at least 10 or 20%, control of inotropic stimulation, for example by transmission of paired or coupled stimulating pulses or bursts only for specific cardiac cycles and not during each cycle, could be considered and the oxygen consumption indices or other indices such as those defined in the earlier documents incorporated by reference, could also be used to check that the increase in hemodynamic performance is not taking place to the detriment of the availability of oxygen for the patient.

In addition, with the improvement according to the invention, the electrical and mechanical results of inotropic stimulation according to the invention will be recorded and processed with those previously acquired for carrying out simulation in order to specify better the particular characteristics of the patient's heart as defined, for example, by the various aforementioned parameters, and this will then allow electrocardiograms and/or electromechanical curves of simulation to be obtained.

Particularly if OIST is applied to patients suffering from grave or acute heart failure, it is found that it may be impossible to start OIST or OIST is disrupted during operation. In order to anticipate and prevent these grave incidents, the cause of malfunctioning of OIST should be carefully analyzed. It is frequently due to inadequate superimposition of the electrical refractory zones (ERZ) and mechanical refractory zones (MMRZ) which can be shrunk or moved relative to one another in such a way that the duration of the effective critical zone (ECZ) is virtually cancelled or, more frequently, reduced, for example to 10 ms. In this case, if the stimulating burst of the OIST consists of pulses with an interval of 15 ms, it becomes impossible to carry out continuous inotropic stimulation and the patient's oxygen reserves are likely to be exhausted.

According to a variation of the invention and in order to avoid this grave failure of the OIST, the time durations and superimpositions of these ERZ and MMRZ should be measured precisely substantially in the same location of the heart and, if necessary, continuously; this function can be performed by the analyzing simulator (ASIM). When the ASIM records a critical shrinkage of the ECZ, it can suitably bring together the pulses of the bursts automatically without delay in an attempt to cause at least one pulse to target regularly within the ECZ. If it is impossible to reach the ECZ regularly, the ASIM is programmed to stop the OIST without delay. A continuous bringing together of the pulses to within 10 ms prevents ERZ measurement, in the current state of electronics, and includes other electronic and possibly physiological drawbacks.

Preferably, the device comprises:
means for continuously measuring electrical refractory zones ERZ in a location of the heart,
means disposed substantially in the region of the heart for precisely measuring the zones of maximum myocardial contraction MMRZ,
the device being arranged so as to acquire, from said means, the temporal superimposition, in the same cycle, of said zones ERZ and MMRZ and determine the common zone known as the critical zone ECZ.

The electrical stimulating means are arranged so as to immediately send at least one stimulating pulse into said region of the heart during said zone ECZ.

As an improvement said means for checking the temporal superimposition are sensitive to a shift between the zones ERC and MMRZ in order to send a stimulating pulse or a burst supplying at least one pulse to the interior of the zone ECZ.

Preferably, said sensitive means enable the time interval between two pulses of a burst to be reduced so as to increase the probability of having a pulse during said zone ECZ.

Preferably, the duration between two pulses of a burst cannot be reduced to less than a value of approximately 10 ms.

Preferably, if it is impossible to cause at least one pulse to travel to the interior of the zone ECZ, the device stops the coupled or paired stimulation.

According to an improvement, the device stores the occurrences and time durations of the zones ECZ during a plurality of cycles and the development thereof is analyzed in order to anticipate any tendency to the suppression of said zone ECZ and, in this case, to implement a treatment, in particular by perfusion of drugs or change of the OIST rhythm in order to act on the duration of the zones ERZ or MMRZ or the overlap thereof.

The means used by the device according to the invention, unless otherwise described, are means which, in their individuality, are conventional in the art and described, for example, in the various documents incorporated by reference.

Thus, the acquisition means combine electrodes, known physical or biochemical sensors with signal shaping means and data processing means, including microprocessors and memories, with software which is known to a person skilled in the art or which he can produce in a routine manner once he has read about the operation described by the invention. The same applies to the means used for stimulation, including their electric power source, and the data processing means which are sensitive, for example, to the rhythms, durations, detection thresholds and electrical or hemodynamic or biochemical curves acquired or produced.

The invention also relates to processes for treating or preventing cardiac diseases comprising the successions of steps described hereinbefore, these processes employing a device as described in the present invention.

In a first practical example, therefore, the invention relates to a process for electrical stimulation of the heart, in particular for treating or preventing cardiac failure and, in particular left ventricular failure or tachycardia, arrhythmia or else for significantly increasing hemodynamic performance of the heart, said process comprising the following steps:

implanting a stimulating device as described according to the present invention;
automatically acquiring information on the heart rhythm, preferably by acquiring the electrocardiogram, preferably with accelerated development;
determining, preferably during each cycle, preferably in real time, the duration of the electrical refractory period (ERZ) following the last wave R of the current cycle or of another nearby earlier cycle;
and, during the following cycle, sending, substantially without delay before the end of said determined refractory period (ERZ), at least a stimulating pulse, preferably a burst of stimulating pulses, so as to induce a significant extension of the refractory period (ZR) without causing any mechanical stress.

In a second embodiment, a process according to the invention for stimulating the cardiac muscle, in particular in the case of one of the aforementioned diseases, comprises the following steps:
automatically acquiring information on the heart rhythm, preferably by acquiring the electrocardiogram;
determining, preferably during each cycle, preferably in real time, the duration of the electrical refractory period (ERZ) following the last wave R of the current cycle or another formerly nearby cycle;
sending, during the following cycle, substantially without delay at the end of said determined refractory period (ERZ) at least one stimulating pulse, preferably a stimulating burst;
automatically acquiring information on the cardiac hemodynamics, preferably the pressure/volume curve of the cardiac contraction;
determining the potentiation of said hemodynamics;
in the case of zero or excessively weak potentiation, modifying the moment of sending and/or the parameters of said pulse or burst until a higher degree of hemodynamic performance is obtained.

In a particularly preferred embodiment, means (4) for determining the duration of the electrical refractory period (ERZ), which are sensitive to the detection of the pulse in a burst which triggered a complex R', and means for determining the maximum mechanical refractory zone MMRZ are used, and a zone ECZ posterior to the electrical refractory zone ECZ [sic] is determined in said zone MMRZ and, if said zone ECZ exists, at least one stimulating pulse is sent into said zone ECZ.

In a particular embodiment of said processes of the invention, the heart is allowed to generate the spontaneous electrical systole R which induces the contractions of the cardiac muscle. The sending of the pulse or the burst or trains of pulses just before the end of said refractory period can thus be said to be "paired" with said spontaneous electrical systole R.

In a further embodiment, which can thus be used optionally together with the preceding embodiment and in particular in the case of bradycardia or else for the orthorhythmic reduction of tachycardia, a stimulating pulse is regularly sent to the heart to induce a stimulated electrosystole R which leads to myocardial contraction and the coupling pulse or the stimulating burst according to the invention is sent substantially without delay at the end of the refractory period, the heart thus being stimulated at an electrical rhythm, said stimulating pulse or burst thus being said to be "coupled" to the electrosystole.

In the processes according to the invention, the duration of the electrical refractory period (ERZ) can be determined by stages such as those described with regard to the operation of the device according to the invention, for example by calculation and/or scanning and/or measurement.

In a particular embodiment of the processes according to the invention, wherein a burst of pulses is sent, the burst of pulses is sent just before the estimated end of the refractory period ERZ, the duration of the burst and the number of pulses being such that an electrical stimulation occurs very quickly after the end of said refractory period (ERZ).

In a perfected embodiment, that pulse of the burst which triggered a wave (R') extending the refractory duration (ERZ) is detected and, if necessary, at least one characteristic of the burst is modified during the following cycle.

These characteristics include, in particular, the instant when the burst began, its duration, the number of pulses, the pulse interval and the intensity of the pulses of the burst.

Preferably, anti-tachycardic stimulation means and extrasystole-sensitive means are also used for automatically stopping said stimulation on the occurrence of excessively great hemodynamic instability and electrical arrhythmia corresponding to preselected criteria.

In addition to the rhythm acquisition means, means for determining the duration of refractory zone and means for transmitting a pulse or a burst, there can be used means (7, 10) which are sensitive to the precise acquisition of the hemodynamics for determining the variations in efficacy of the hemodynamics, these means being capable of controlling the transmission and optionally the parameters of the pulse or the burst, preferably in a manner resembling that which produced the hemodynamics which are most favorable for the patient at a given moment.

Said means act on parameters such as: a programmed ventricular rhythm and/or an automatic adjustment of the beginning or end or duration of the burst or the number or the characteristics, in particular width, intensity, polarity, density, interval of the pulses in the burst, or else a location of the transmission of the burst at one or more stimulating electrodes.

Preferably, metabolic parameters, in particular of oxygen consumption and/or the equivalents thereof such as the measurement of electron densities of myocardial cell membrane or increase in ketone bodies, lactic acid, etc. are acquired.

In a perfected embodiment of the process, a stimulating pulse or burst is sent into the zone (MMRZ) situated within the plateau of the contraction curve of the mechanogram and during which the contraction of the myocardium is substantially at its peak.

Thus, the stimulating pulse or at least a stimulating pulse of a burst falls within said zone MMRZ. Preferably, said zone (MMRZ) is acquired automatically.

In an embodiment, the intracavitary pressure is measured by a sensor and a zone of maximum pressure is selected in the systolic plateau of the cardiac mechanogram in which the transmission of a stimulating pulse or burst is induced.

Preferably, however, the local intramyocardial pressure is measured in the vicinity of a detecting and stimulating electrode.

Preferably, the myocardial pressure is detected in the intra-auricular and/or intraventricular septum.

In a further embodiment, the variation in the volume of the heart or a part of the heart is measured by detecting the zone where said volume has reached and maintains its minimum value.

The invention also relates to a process wherein:
information relating to a patient's electrocardiogram, including the heart rhythm, is acquired,
information relating to the patient's hemodynamic performance is acquired;
and this information is used to simulate the effect of prolonged inotropic paired or coupled stimulation.

Said acquired information relating to the patient's hemodynamic performance is compared to the simulated effect on said performance of an inotropic paired stimulation.

Preferably, the information is acquired and compared cycle by cycle.

Preferably, at least one of the following parameters relating to cardiac contraction is measured:
gradient (dp/dt) of the phases of ascent and/or descent of the intracavitary and/or intramyocardial pressure;
duration of the systolic pressure plateau, corresponding to systolic ejection;
duration of the systole (cardiac contraction);
duration of the diastole (filling phase);
ratio between the diastole and systole durations;
quality of the diastole, in particular filling depression or speed and amplitude of the fast and slow phases;
electromechanical coupling (period separating the beginning of a QRS complex from beginning of the mechanical systole which it causes);
shift between the local intramyocardial contraction curve and the global intracavitary contraction curve.

Information relating to the electrocardiogram and to the hemodynamic performance of a simulation of inotropic paired or coupled stimulation is compared with corresponding information acquired during a subsequent identical or similar actual inotropic stimulation.

Preferably, a threshold level for values of the information on the simulated hemodynamic performance of the patient is acquired or calculated and, if the threshold is exceeded, an identical or similar inotropic paired or coupled actual stimulation is triggered.

Preferably, the information relating to the patient's electrocardiogram and to the patient's hemodynamic performance is acquired at different rhythms, in particular rhythms which increase or decrease by increments or progressively.

Preferably, there are used means which are sensitive to said acquisition means arranged so as to simulate the effects of a plurality of inotropic paired or coupled stimulations at different heart rhythms.

Preferably, said comparison is effected for a limited number of cycles of the actual inotropic stimulation and, if the absence of a satisfactory hemodynamic performance level is observed, the current inotropic stimulation is terminated.

If an adequate initial increase in hemodynamic performance is observed, inotropic stimulation is continued and it is detected whether the initial increase in hemodynamic performance is maintained and/or still increases progressively for a greater number of cycles.

The effects of cardiovascular target medicaments, which have previously been administered or are being administered, are used in the analysis.

Preferably, the differences between the simulation and stimulation curves are emphasized visually and/or quantitatively, in particular by superimposition of the curves.

Preferably, the cardiac mechanogram is acquired, in particular until the appearance of a cycle which is long enough to obtain a good myocardial contraction, and a stimulating pulse or burst is then transmitted at an instant within the plateau of the mechanogram curve (MMRZ), in particular just before the end of the electrical refractory zone (ERZ), after which stimulation is carried out immediately after the end of the electrical refractory zone which will cause a new electrical refractory zone.

Advantageously, a first threshold of increase in global hemodynamic performance/mn and/or per cardiac contraction can be defined, in particular the cardiac output, said threshold being equal to at least 15% or preferably 25% of the performance prior to treatment, and the stimulation parameters are adjusted until at least said threshold value is obtained.

If the increase according to said first threshold value is not obtained during a period of approximately 1 to 10 contractions, it is preferable to stop the treatment.

The invention also relates to a process for treating acute or severe heart failure wherein:
the heart rhythm and, in particular, the interval between at least the last two waves R (induced or spontaneous) of a cardiac cycle which has just been completed are automatically acquired,
the duration of the electrical refractory period (ERZ) following the last wave R of said cycle is determined, preferably continually,
at least one stimulating pulse and preferably a stimulating pulse burst is sent substantially without delay at the end of the refractory period (ERZ), the duration of the burst being such that, in view of the pulse repetition interval in the burst, a stimulating pulse of the burst is sent to the heart substantially without delay after the end of the refractory period, and
these steps are repeated for a series of at least three contractions if an initial improvement in cardiac performance is observed, and
and, in the absence of an improvement, the process is automatically stopped.

Advantageously, the total mechanical performance of the heart, in particular its blood flow and/or the variation in ventricular volume are compared, on the one hand, before carrying out the steps of the process and, on the other hand, after carrying out the steps of the process and, if the increase in heart performance is greater than 15%, the steps of the process are carried out again.

The invention also relates to a process for cardiac resuscitation in a patient suffering from severe or critical heart failure wherein:
the heart rhythm and, in particular, the interval between at least the last two waves R (induced or spontaneous) of a cardiac cycle which has just been completed is automatically acquired,
the duration of the electrical refractory period (ERZ) following the last wave R of said cycle is determined, preferably continually,
at least one stimulating pulse and preferably a stimulating pulse burst is sent substantially without delay at the end of the refractory period (ERZ), the duration of the burst being such that, in view of the pulse repetition interval in the burst, a stimulating pulse of the burst is sent to the heart substantially without delay after the end of the refractory period, and
these steps are repeated at least until an at least progressive improvement in detectable cardiac performance is achieved.

The treatment and resuscitation processes can advantageously also employ the other steps of the processes described hereinbefore.

The invention also relates to processes for the treatment or prevention of cardiac arrhythmia, in particular spontaneous cardiac arrhythmia, employing the steps enumerated hereinbefore for application of the device for preventing arrhythmia. It also relates to processes for treating or preventing cardiac arrhythmia caused by or associated with the use of a device according to the invention, said process employing the corresponding steps enumerated herein before.

Regeneration of the Myocardium

The invention also relates to a process for physiological and/or anatomical and, in particular, cellular regeneration of the myocardium in the case of heart muscle failure, this process preferably comprising the steps described herein before.

A process of this type according to the invention comprises the following steps:
implanting in the heart, in particular in a right or left atrium and/or a right or left ventricle, regeneration cells, in the subendocardial or intramyocardial position, preferably in a plurality of groups of cells or in a cell blanket or cell mesh,
and carrying out stimulation according to the invention, preferably paired stimulation.

A process of this type according to the invention comprises the following steps:
obtaining and cultivating, in vitro, regeneration cells, preferably in the form of small groups;
placing the confluent cells in electrically conductive contact with one another and with an electrical stimulation device,
periodically sending electrical pulses to said cultivated cells;
detecting the electrical responses of the depolarizations and repolarizations or membrane potentials of the cultivated cells, said cells being intended to be implanted in the heart, preferably in a plurality of groups or sheets of cells, in a subendocardial or intramyocardial position, once the electrical detection thereof by intracellular microelectrodes has demonstrated the cell capacity for rhythmic electromechanical activity adapted to the recipient's myocardium.

The stimulation can be a mere electrical stimulation having a rhythm which preferably resembles the normal heart rhythm. It can, preferably after an initial period, be sent in a paired or coupled form, once the groups of cells in culture are synchronized and manifest an acceptable electrical refractory period relative to the recipient's myocardium.

The cultivated cells may be of any type, for example muscle, myocardial, embryonic cells or stem or totipotent or multipotent cells.

These cells may also have been obtained by a process wherein a nucleus or a part of nuclei or of foreign chromosomes or genes are transferred into a functional oocyte or a totipotent or multipotent or embryonic stem cell and this nuclear material is removed at an incomplete stage of mitosis for transfer into a totally or relatively differentiated, preferably original or autologous, cell.

Regeneration can also relate to vascular, for example coronary, parts employing such means with adapted stimulation for coronary functioning.

In order to accelerate and prolong the multiplication thereof in vitro or after transplantation, these cells or some of them, for example myocardial or muscular precursor cells or others, can be genetically modified so as to over-express telomerase or Sir2 protein, in particular by transfection with a viral or retroviral vector or other vector, of the gene of telomerase or reverse transcriptase Sir2 protein (hTERT) by employing, for example, the method described by Steven Goldman, Nature Biotech., Feb. 16, 2004.

The OIST according to the invention also applies to the at least partial regeneration of the cardiac muscle, in particular in patients suffering from chronic or acute heart failure, by employing the OIST, even in the absence of cell contribution, continuously or periodically for a long period of, for example, from a plurality of weeks to a plurality of months or more.

The invention also relates to a process for preparing living cells, in particular vegetable, animal and human cells, which can be reimplanted prophylactically or therapeutically, wherein a nucleus of a dedifferentiated cell is transported in an oocyte, preferably an unfertilized or recently fertilized oocyte from a homologous or heterologous mammal, previously preferably completely or partially freed of its nucleus, so as to induce a stage of mitosis of the transferred nucleus, in that this nucleus is removed during the mitosis and before the end of it, then this nucleus which is partially dedifferentiated in mitosis at this stage is introduced into a cell, preferably after some part or the totality of his nucleus or its nuclei have been removed from it, so as to induce and terminate the differentiating nuclear division thereof and to form a cell strain or a tissue at a less advanced stage of differentiation than said differentiated cell.

The transferred nucleus can be extracted during the metaphase, anaphase, prophase or telophase of the first mitosis.

A nucleus of myocardial, muscle or cardiac auto-rhythmic cell, in particular sinusal cells from the Tawara's node or fibers from the His' bundle or Purkinje bundle can be transferred into the oocyte.

The partially dedifferentiated cells obtained can be subjected, preferably after or during the cell multiplication culture thereof after the formation of a confluent assembly, to periodic electrical stimulation of the cardiac stimulation type, in particular by the stimulation process according to the invention.

Preferably, said cells are subjected to coupled or paired electrical stimulation in which that pulse without a contractile effect is sent just after the end of the electrical refractory period of the cells in culture.

For example, said cells are subjected to electrical stimulation in cycles comprising a first stimulating pulse and, toward the end of the refractory period, a pulse train, so that at least one of the pulses of the burst falls just after the end of the electrical refractory period of the cells and during their mechanical refractory zone of maximum contraction.

The cells obtained by this process can be implanted in the region of the auricular myocardium, in particular in the case of a patient suffering from auricular fibrillation.

The invention also relates to an arterial segment or stent, in particular with a coronary, aortic, carotid, renal or femoral target, comprising a structure which is coated or colonized by cells obtained by the process according to the invention, preferably consisting of living, autocontractile and elastic, in particular autologous cells, cultivated by the process.

This arterial segment or stent can be shaped in the manner of an arterial stent arranged so as to be introduced into an arterial lumen.

Preferably it comprises means for electrical stimulation of the arterial type, coordinated with the ventricular diastole, of said cells of the segment, for example at least one stimulating and/or detecting electrode.

The stimulating and/or detecting electrode has preferably been introduced into the cell culture so as to be surrounded by said living cells.

The segment or stent can comprise a sensor, in particular for measuring oxygen saturation and/or metabolic parameters and a detecting or stimulating electrocardiographic sensor.

It can have a plurality of electrodes arranged for obtaining variations in the local electrical impedance.

Preferably, it comprises a structure, in particular in expansible meshes supporting different cell layers, such as endoartery, myoartery and periartery structure, said structure allowing a spontaneous increase with progressive widening of its lumen and creation of vascularization which nourishes, in particular, the myoarterial portion.

The structure is produced from at least one of the following materials: PLGA, collagen, globin, for example by knitting.

It is also possible, for example, to provide an arterial stent without living cells having a structure which is radially expansible but sufficiently rigid to keep the arterial lumen open at least in systole, which is optionally biodegradable or removable by a catheter and capable of receiving a physiological stent as described.

Finally, the invention relates to a biological cardiac pacemaker comprising partially dedifferentiated auto-rhythmic cardiac cells or tissues according to any one of examples 110 to 122 (which appear at the end of the written description hereof) which is preferably autologous or homologous and originates from the recipient's organism and is intended to be implanted in the heart or in a defective region of the heart.

The invention will be described hereinafter with reference to the accompanying drawings in which:

FIG. 10 shows schematically the electrocardiograms and mechanograms used in the stimulation according to the invention;

Figure 1:
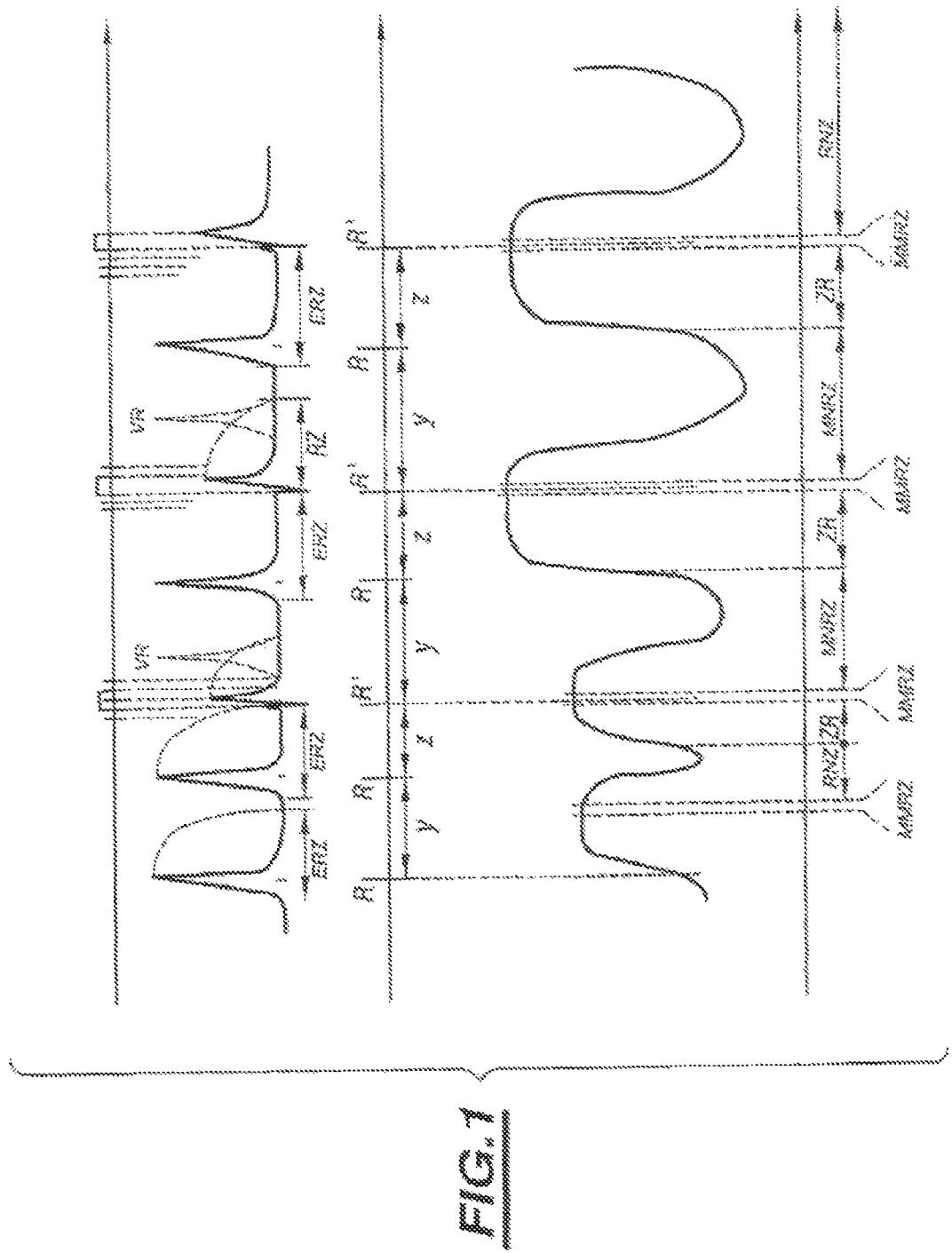
FIG. 1 shows schematically an electrocardiogram associated with a mechanogram of the myocardium corresponding to the operation of a device according to the invention.

FIG. 1 shows an example of the operating principle of a device according to the invention. The upper line shows the ECG, the median line shows the couplings Y of the orthorhythmic bursts relative to the waves R of the basal rhythm, in other words as a percentage of the duration of the earlier cycle Z and the lower line shows the myocardial mechanical activity. The waves R in solid lines show the spontaneous or stimulated depolarizations and the waves RV in broken lines the basal waves R inhibited by the artificial extension (ZR) of the refractory zones induced by the bursts of electrical pulses. The stimulations in bursts of five pulses of the stimulator according to the invention are shown clearly on the ECG and the first pulse of each burst, which causes depolarization, allows each functional refractory zone (ERZ of RZ) in each cycle to be measured. It should be noted that the beginning of the electrical non-refractory zone (ENRZ) precedes the beginning of the mechanical non-refractory zone (MNRZ). On the mechanogram, the interval MMRZ corresponds to the maximum contracted systolic refractory zone which is still active and during which propagated electrical stimulation causes in practice neither a myocardial effect nor myocardial energy expenditure because this muscle, which is in maximum contraction just before its active relaxation, is incapable of any other expending biological action. The MMRZ is followed by the mechanical non-refractory zone (MNRZ). It should be borne in mind that any electrical stimulus occurring immediately after the MMRZ, for example 20 ms later, falls in the MNRZ zone and can already cause a premature biochemical energy recharging reaction for this incipient diastole, leading to oxygen consumption even in the absence of mechanical activity perceptible by current instruments.

The MRZ or RZ interval corresponds to the mechanical refractory zone preceding the narrow zone MMRZ. The zone MMRZ corresponds only to a small portion of the peak of the ventricular systolic pressure curve.

The reference character D designates the electrical diastole.

The foregoing static description of the functional zones of each cardiac cycle does not show the actual dynamic progress in the region of a suffering myocardium. In reality, the various functional zones and, in particular, the ERZ and MMRZ can vary from one cycle to another, for example between 15 and 18 ms; this is already partially promoted by cardioactive medicaments, the vegetative dynamism and by the variations in the pre and post charges, transmembrane fluxes and other intracellular metabolisms. It will now be understood why the conventional paired stimulation which uses only a single electrical pulse to prolong the ERZ, with a constant coupling interval in ms, cannot produce an OIST of clinical certainty because the only fixed coupling stimulus will fall before, during or after the mobile critical interval, which remains invisible on a normal ECG. This results in physiologically inconstant cardiac stimulation, which is visible only on special ECGs having a high speed of development and on very precise intracardiac mechanograms (which are not found in conventional coronary angiography), and specific metabolic requirements, leading to an over-consumption of oxygen which is detrimental to the myocardium, the hemodynamics and the eurhythmia and is wrongly attributed to mere paired stimulation.

Not only the durations of the refractory zones but also the excitability thresholds can vary during OIST cycles treated by the invention with paired or coupled stimulation. To instantaneously and continually compensate for these irregularities, an automatic device for instantaneous readjustment of these thresholds which are well-known in the field of implanted cardiac stimulators first described by the inventor in his French patent No. 1,237,702, P.V. No. 651 632 of Jul. 11, 1953, should be provided. It may be beneficial to launch periodically and automatically on demand, depending on the frequency of the critical variations of the observed thresholds, orthorhythmic bursts of which the voltage varies progressively or otherwise and of which the effects on the electrical depolarization caused will automatically be taken into consideration for readjusting, for example, the intensity of the pulses making up each burst in the next cycle concerned. In addition, this intensity of the pulses can vary regularly or otherwise from one pulse to the next or periodically within each burst of the OIST. In the case of specific significant variations in these excitability thresholds or refractory zones, it is desirable to automatically check whether the variations merely relate to one of the parameters and which, or whether both parameters vary together and how. These checks also allow an instantaneous preventive reaction if it is impossible to continue stimulation (OIST) according to the invention as programmed, for example in the case of metabolic disorders (incipient local lack of oxygen, tendency to arrhythmia, lowering of hemodynamics, etc.). In the more frequent cases of OIST, which remains sufficiently stable, the number, the density (a plurality of electrodes or a large-area electrode emitting by focusing on a receiving electrode), the width or the intensity of the pulses of each burst of the new orthorhythmic pacemaker can, for example, automatically be reduced or, conversely, be increased in the case of increasing instability. It is thus possible to obtain automatic exploration of each cardiac cycle which is continuously adapted to its own pathophysiological development and allows numerous cardiac failures to be instantaneously prevented, treated and notified, these cardiac failures otherwise being revealed later or too late. In addition, this process can allow the instantaneous control of specific implanted medical pumps (Zacouto, U.S. Pat. No. 5,305,745) and, if there are a plurality of electrodes, which are preferably quite spaced, for stimulation in the heart (for example, ventricular resynchronization stimulation), a sudden adequate difference between these refractory zones and the excitability thresholds can indicate a coronary thrombosis or local myocardial lesion. The diagnostic functions of the OIST according to the invention can themselves justify the application thereof, for example when using drugs which influence cardiac function, as required by cutting off the stimulation functions.

A distinction should be made in clinical use of OIST depending on whether it is applied to tachycardia or myocardial failure. In the case of poorly tolerated, refractory or recurrent tachycardia, OIST allows, after installation of the cardiac stimulation electrodes, the rhythm thereof to firstly be reduced rapidly by approximately two-fold with a considerable immediate increase in the heart output, which is due on the one hand to the great prolongation of the diastole and, on the other hand, to the PESP which is added thereto. In certain clinical cases, in particular ventricular tachycardia (VT), it is possible to eliminate this tachycardia by cutting off their reentrant circuits by the adjustable orthorhythmic bursts of the OIST which can automatically target the smallest myocardial spaces not yet in the refractory phase during ectopic depolarization. It is not always enough to subject a VT to OIST in order to reduce it, but once installed, its orthorhythmic parameters must be varied, for example the pulse intervals, the numbers, intensities and widths thereof, the coupling percentage relative to the duration of the earlier cycle, etc. of the bursts must be brought closer together and, if necessary, the stimulating electrode must be brought closer from the starting point of the ectopic activations; all this can be achieved and stored automatically, for example relative to the marking spikes of the detections and stimulations of the orthorhythmic pacemaker (ORP), if there are a plurality of electrodes which thus allow an electrical shock to be avoided. In the case of acute or chronic cardiac insufficiencies not caused by rapid ectopic tachycardia, which are frequent in moderate sinusoidal tachycardia, the OIST immediately causes a reduction in the rhythm (for example 100 per min to 60 per min) and a significant lasting increase in the cardiac and coronary output as well as an immediate lasting reduction in the pulmonary arterial pressures. it can preferably In the event of irreducible or recurrent tachycardia, in particular VT, the rhythm thereof can be reduced by half by using a continuous OIST, and this can be an alternative to an ablation or can allow one to expect an ablation under excellent hemodynamic conditions, without danger to the patient, and this cannot be achieved even by a return to the sinusal rhythm. In wearers of an implanted automatic defibrillator (IAD) it is possible on the occurrence of a dangerous, resistant or excessively recurrent tachycardia during conventional orthorhythmic anti-tachycardic stimulation, to switch firstly to an OIST and, only if good hemodynamics are not re-established after about 10 seconds, to trigger the defibrillation shock; this procedure will allow painful shocks to be eliminated. In the case of acute or chronic cardiac failure, not caused by rapid ectopic tachycardia, which are frequent in moderate sinusal tachycardia, the OIST immediately causes a significant lasting increase in the cardiac and coronary rate as well as a lasting reduction in the pulmonary arterial pressures. A further advantage of the implanted OIST is that it generally allows the patient to resume much greater physical activity. The abrupt significant increase in hemodynamics caused by an OIST can be a drawback for some patients; in these cases the OIST can be programmed not to launch its bursts or pulses prolonging the zones ERZ for example only at a spontaneous or stimulated wave R at three or four instead of one in two or again to reduce the duration of the diastoles by accelerating the basic rhythm. For example, the mode of paired stimulation of the OIST can be switched automatically to coupled stimulation by the intervention of a program entailing an increase which is strictly limited by a selected threshold. A coupled stimulation is a stimulation without any spontaneous wave R at a rhythm which is totally imposed by the OIST. These two modes can occur automatically if they are controlled relative to the parameters of the desired hemodynamics and preferably by controlling the concomitant metabolic changes such as the oxygen consumption.

A further known advantage of the orthorhythmic pulse bursts used by the OIST is that, with a burst, for example, of four successive square pulses having a duration of 0.5 ms each at 1.4 volts with a pulse interval of 15 ms, if the second pulse causes depolarization, the following pulses will rapidly exceed (propagation rate exceeding several Km/sec) possible fibrillation which has been beginning locally for less than 15 ms (propagation rate of approximately 70 cm/sec) and will surround it with a refractory zone; in addition, the first pulse of the burst which falls in ERZ eliminates the propagation of possible depolarizations of a few earlier cells which are invisible on the ECG but can sometimes trigger an arrhythmia.

Figure 2:
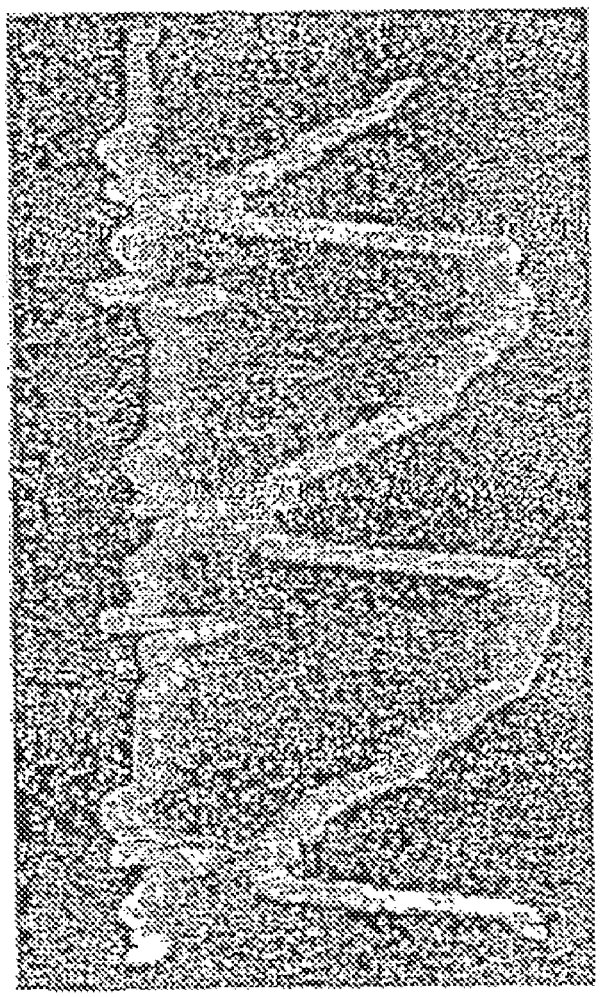
FIG. 2 is a view of an actual example.

In addition, the OIST immediately improves the coronary flow, particular by intervention of the EPR and by the highly elongated diastole, as known in coronary angiography and by the motor beginning of the diastole which is increased proportionally to the potentiated shrinkage of the myocardium caused by the intensified contractility which corresponds to a marked increase in the viscoelasticity of the myocardium during the motor phases; this viscoelasticity is measurable, for example, by a multiaxial pressure detector implanted in the myocardium, such detectors being known. The concomitant drop in the pulmonary arterial pressures is probably due, in particular, to the rise in heart rhythm. In theory, the OIST should not lead to a significant additional expenditure of oxygen. The significant deceleration of the ventricular rhythm reduces this oxygen consumption whereas the increase in contractility demands an oxygen supplement, despite an improved energy output. A specific increase in oxygen consumption during the OIST also corresponds to an increase in the ratio of heart output to consumed oxygen output; the sudden increase in the coronary flow will usually allow this supplementary oxygen expenditure to be tolerated well. With equal increase hemodynamics, the OIST consumes less oxygen than the other heart rhythms. There are extrasystolic spontaneous ventricular rhythms with optimum hemodynamics which function as a paired artificial stimulation as if the maximum contraction causes a targeted electrical extrasystole for protecting the myocardium from a next contraction which is too close (FIG. 2) recorded by the inventor and published (Dtsch. Gesellsch. Kreislauff. 29 Congress, pp 255-261, 1963 Steinkopff Verlag Darmstadt). A further example of spontaneous rhythm resembling a paired stimulation is the electromechanical decoupling, one QRS in two, in the event of rapid tachycardia; this phenomenon can last for years, and patients are often well and are surprised when their tachycardia is revealed to them.

The OIST according to the invention aims to take optimum control of the rhythm and contractility of the heart, on the one hand, by occupying the very first beginning electrical non-refractory zone of a cardiac cycle and, on the other hand, by attempting to assure optimum contractility and a desired blood flow per minute; this last contention necessitates geometric and/or volumetric and energy control in real time of at least one cardiac ventricular cavity. For this purpose and for ORP with OIST, whether or not implantable, it is preferable to provide a device demanding little energy, for example of the intracardiac electrical impedance measuring type. The parameter of development of the volumetric variations is preferably completed by that of the intracavitary blood pressures and/or concomitant intramyocardial pressures, in order to reproduce a correct pressure/volume curve which can preferably be displayed at the exterior of the body by conventional telemetry. For an automatically programmable stimulator of this type, it is possible to produce an electronic device which incorporates, for example, the areas of the pressure curves and, if possible, corresponding volumes and rates and blood flows (for example by intracardiac electrical impedance measurement type), relative to the programmed ventricular rhythm, and which then entails a rhythm close to the value which detected the most favorable hemodynamics for a given patient at a given moment, after having performed, stored and compared these values obtained after a specific frequency scanning (Zacouto, U.S. Pat. No. 5,306,293). In addition, automatic adjustment of the pulses constituting the ortho-rhythmic stimulating burst relative to the hemodynamics and/or to the oxygen consumption can vary the number of pulses, throughout their interval, which may be non-equidistant, their width, their shape, their polarity, their intensity and their voltage which may also be unequal as well as the location of the application thereof in the heart region. This location of their application can comprise fixed or variable monopolar, bipolar or multipolar stimulations with endocavitary, intramyocardial, epicardial, auricular or ventricular electrodes or coronary intravenous, coronary intra-arterial or intra-stent electrodes such as special stents with ECG and/or stimulating electrodes with or without hemodynamic sensors or sensors of oxygen and/or $CO_2$ saturation, pH, glycemia or other metabolic indicators. To avoid a high expenditure of energy by the electronics of these implanted apparatus, a small HF aerial can be installed on either side of the skin to transmit additional energy when the apparatus uses special therapeutic sensors and effectors.

The control of the heart rate by the OIST according to the invention allows an accelerated heart to be accelerated and also decelerated, and this also distinguishes it from conventional cardiac pacemakers. In the event of OIST-induced relative bradycardia, the electrical non-refractory phases are less prolonged than with spontaneous bradycardia. If it is not possible to obtain the desired adjustment of the accelerated ventricular rhythm with the paired stimulation, the OIST can automatically pass to ventricular coupled stimulation and this eliminates any spontaneous QRS complex and allows an effective ventricular rhythm which is half of the stimulated rapid ventricular rhythm to be obtained. If the atria and Hisian conduction are normal, the atria can be brought to a rapid rhythm of approximately 160 per min and ventricular OIST can be obtained at about 80 per min, as successfully achieved on two patients suffering from cardiac failure, and this enables a driven but quasi-normotropic to continue in its activation, as viewed from the ventricle.

Outside regular tachycardia, the reduction of the non-refractory phases in the myocardial space produced by the OIST and its adjustments give this cardiac stimulation an anti-arrhythmic effect, in particular for eliminating early ventricular extrasystoles. In the event of auricular fibrillation (AF), the ventricular OIST could allow the ventricles to be protected from the influxes of the AF completely in the case of influxes of the AF which fall early in the ventricular cycle (VC) and partially in the case of the influxes occurring later in the VC, if necessary by potentiating with specific drugs which decelerate His' conduction, and this gives back to the ventricles a sufficiently regular rhythm, for example eliminates all VC of less than 600 ms, which is partially adjustable and accompanied by optimum contractility; this can compensate and over-compensate the unfavorable effect of the AF on myocardia which are fatigued by tachyarrhythmia and low coronary flows and can optionally potentiate the effect of digoxin and other cardioactive medicaments.

A ventricle can also be stimulated toward 150 pulses per min and obtain, by OIST according to the invention, an effective regular rhythm of about 75 pulses per min which is well tolerated and sheltered from the influxes of the AF. An auricular OIST increases the auricular contraction to a maximum and potentiates its muscular power, opposes the dilatation thereof, thromboses, the reinstallation of specific AF (auricular fibrillations) and improves the ventricular and coronary flows if the parameters of the OIST are well adjusted relative to the natural or artificial auricular and ventricular activations. An auricular stimulation can, for example, be achieved in bipolar mode using electrodes placed on the upper half of the auricular septum and capable of helping to synchronize the atria without affecting the ventricles. A double coordinated auricular and ventricular OIST which increase the coordinated auricular and ventricular contraction to a maximum, may be very beneficial, with or without His' partial blockage, for considerably increasing cardiac hemodynamics without delay and for a long time.

Any OIST adapted according to the invention regenerates genetic functioning with inotropic effect of the myocardium with changes of developmental gene expression, ion channels and contractile functions induced by the increased mechanical and metabolic stresses imposed; they will lead to its intracellular remodeling of functional recovery, for example in the event of cardiac failure (dilatations) or necroses (shrinkages). This etiological therapy of each cardiac failure can give a rapid genetic involution of its pathological process and genetic change of physiological and anatomical regeneration caused by the effect of the highly increased contractility to the specific evolutive possibilities of each patient, automatically adapting to each particular case unless specific illnesses, such as metabolic, tumoral, viral, toxic, etc. illnesses prevent myocardial function from re-establishing. The maintenance of cardiac function re-establishment demands adequate peripheral muscular activity which should be coordinated with the central myocardial action of the OIST.

For specific expansive necroses or fibroses of the myocardium, the local autologous grafting of stem cells which are multiplied and differentiated in vitro or of cells which are genetically modified or reprogrammed by mechanical, electrical and biochemical driving capable of recolonizing the destroyed sites and metabolizing specific scar tissues can be envisaged.

It is possible to proceed with the mere local recolonization of partially dedifferentiated isolated cells of myocardium, which is a syncytium, cells which are genetically oriented toward rhythmic and contractile functions with refractory zones which can easily organize themselves, owing to the effect of the environment, into mechanically powerful networks which are well coordinated with the heart.

Preferably, prior programming of the OIST will be added. The in vitro multiplication of the cells to be grafted need not always take place in the immobile state, but preferably also under a controlled alternating mechanical stress which is adapted to the future functions of the cells and capable of inducing an electrophysiological membrane state which is compatible with the function of the heart to be served and is preferably controlled by an OIST adapted to the functional capacity of the cells so as to orient them genetically toward their future contractile function, if possible with autologous serum.

Figure 4:
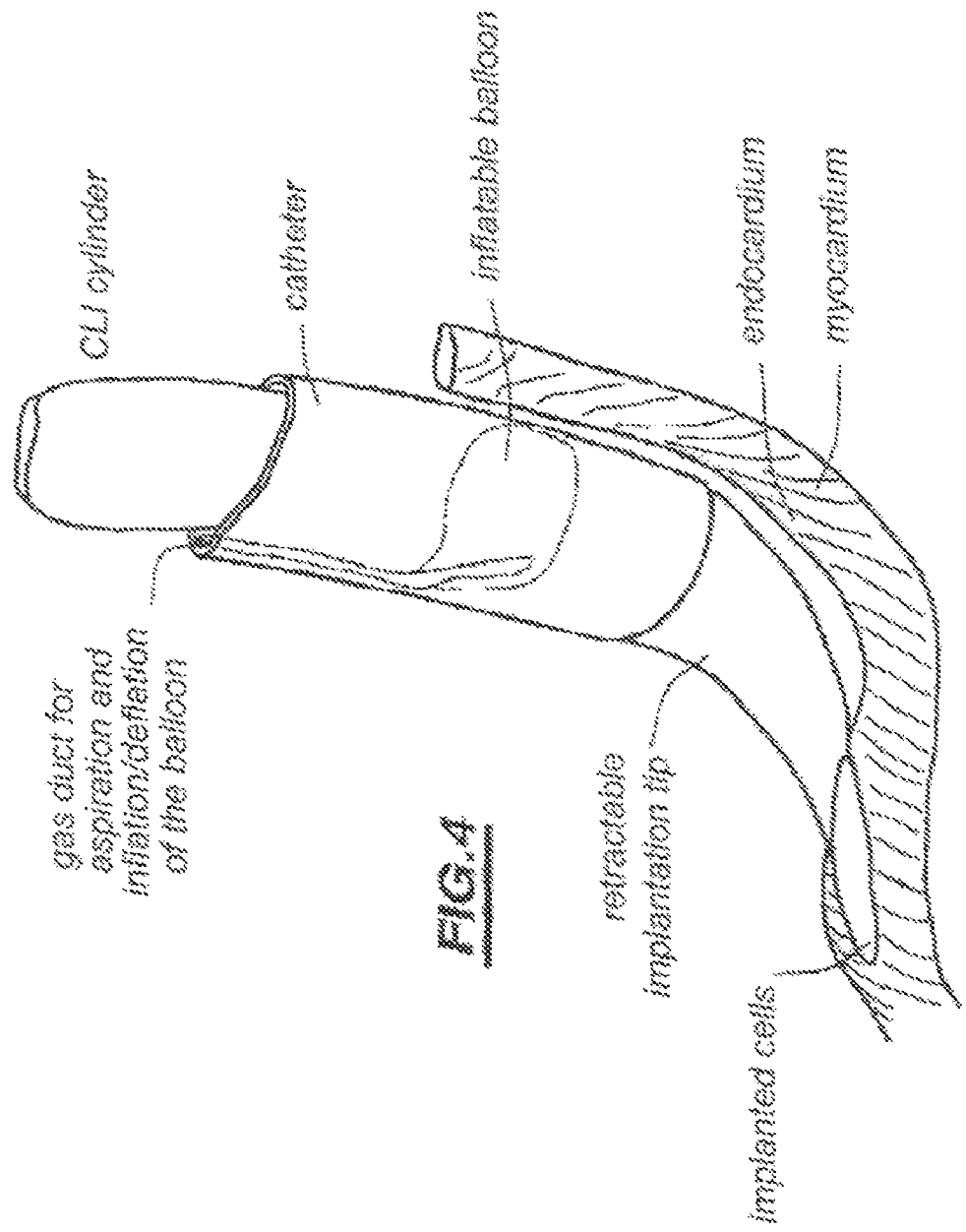
FIG. 4 is a schematic view of a cell implantation device.

In addition, these cells should be incited not all to multiply separately but, for example, to form small functional structures in three dimensions by cultivating them, for example, on a pre-formed, porous, elastic and biodegradable matrix such as PLGA and PLA (polylactic acid derivatives) so as to avoid the dissemination thereof after the injection thereof and to promote the contractile function thereof in a syncytium coordinated with the stimulation of the heart. The small preformed matrices may have 3D shapes which promote their assembly with one another and with the recipient's myocardium, for example in the form of strips, discs, squares, crosses, serpentines, etc. Electrophysiological analysis of these cells should also be carried out prior to implantation, for example by means of intracellular microelectrodes, to verify the refractory zones and the action and membrane potentials and to check their motor capacity, for example by measuring the deformations of their elastic matrix. These cells, which are prepared for their contractile function, can also serve in the case of AF to form a myocardial tissue which can be implanted in the atria and can be produced, for example, through a catheterized venous channel under at least echocardiographic control, the probe or probes also being able to pierce through the auricular septum and also seed the left atrium; this sub-endocardial seeding of groups of implanted myocardial cells either one by one or as a bridge between a plurality of roots with care to avoid perforating the wall and detachable protrusion in the auricular cavity, can be carried out using an orientable catheter equipped at its end with a cylinder containing a narrow flexible pointed retractable tip of the catheter sliding on the endocardium and raising the endocardium by aspiration and pricking it very slightly at this point by pushing a cylinder of cells to be implanted (CLI) into the small fissure obtained by means of a piston which is fully pushed and is retracted against the catheter walls, for example in the form of a valve with resilient lips moved by the pressures or by means of an inflatable and deflatable balloon capable of disconnecting the CLI, the retraction or deflation revealing a new "cylinder" of cells of which the length can be adjusted from the exterior in front of the piston or balloon in the catheter by pressure of a fluid (FIG. 4). The groups and bridges of implanted cells (CLI) will expand and form a network of contractile meshes controlled by a mere OIST or stimulation, for example situated in the right atrium and the CLI, owing to their proximity, should fuse in the original syncytium where they induce certain parts of their genetic equipment. A cell implantation catheter of this type can be applied to any region of the heart and other organs such as kidneys, pancreas, liver, etc. This principle of implantation of multiplied autologous cells capable of multiplying easily and prepared for a contractile function can also be applied to the construction of a complete or partial artificial heart formed at least in part by autologous cells cultivated, preferably, from partially dedifferentiated myocardial cells.

In a preferred embodiment of the invention there is carried out partial cellular therapeutic cloning which consists in introducing into a denucleated oocyte, a total or partial foreign nucleus and removing this nuclear material at a desired incomplete stage of its mitosis and then implanting it in a preferably autologous, differentiated cell which is denucleated or otherwise and in which the initial mitosis will end, leading to partial dedifferentiation.

Purely nuclear partial cloning involving removing the cell nucleus during selected incomplete mitosis of the oocyte before the initial complete cell division at a given instant by analysis, for example optical analysis, of the development of the nucleus can be considered. Thus, for example, during the prometaphase, if light dedifferentiation is desired or, during the anaphase or the telophase, if more pronounced differentiation is desired. Next, it will be introduced into a living cell membrane which is preferably emptied of its nucleus and is preferably autologous, embryonic or from stem cells, for example dermal, epithelial, lymphatic, conjunctive, osseous, cartilaginous, blood or muscular cells. These cells, resulting from incomplete cloning, could then be introduced into a myocardial cell where it can perform regenerating genetic transcription and expression capable of inducing, at least locally and temporarily, in its environment, partial genetic action and contamination to the desired extent.

In a variation of the invention, a nucleus which is already undergoing incomplete mitosis or even complete mitosis, spontaneously or by known artificial provocation, can also be introduced in the form of two initial cells in order to obtain partial dedifferentiation more easily.

In view of the rarity of human or mammalian oocytes, it is considered to render an oocyte multiparous by introducing into it a new nucleus after having delicately removed the first nucleus which is undergoing partial mitosis. This multiparity by successive intraoocyte inoculation may have a dedifferentiation effect on the nuclear material which is different from that obtained during the initial introduction of the nucleus or chromosomes or genes of this same oocyte.

A nucleus which is, for example, already undergoing partial spontaneous or induced mitosis, or otherwise chromosomes or genes or a part of nuclei to be treated in an embryonic cell can also be introduced into the oocyte. This will preferably be of the same tissue, for example myocardial tissue, preferably partially denucleated and cultivatable in vitro, in vivo or in situ. The cell or cells will be cultivated for multiplication, preferably for sufficiently long in vivo in embryonic tissues to obtain partial dedifferentiation. The nuclei thus treated may be left, either in the embryonic cells to constitute a tissue which can be grafted into the organism originating from the nucleus or extracted from their accommodating cells so as to induce local cell regeneration in the region of a differentiated, preferably autologous and identical tissue. Implantation of the nucleus or nuclear portions can also take place within a stem cell, preferably of the embryonic or fetal type.

Partially and selectively dedifferentiated cells of this type may then be introduced into surviving myocardial cells which are preferably original and have preferably been more or less denucleated and can act as regenerating myocardial tissue to be implanted, for example, in regions which have been subjected to sclerosis by fibrosis and are poorly vascularized or regions of the heart having inadequate contractility.

From a certain degree of dedifferentiation, these cells lose their immunogenic power and can be used to regenerate non-autologous myocardial tissues.

This function also comprises the capacity of these genetically activated cells to act remotely by secretion, liberation or induction, in particular through specific biochemical molecules. This transhumoral genetic activation shows, among other things, the capacity to mobilize locally appearing pro-generating cells as observed in extensive myocardial infarction.

This cell preparation, which also applies to other cell types, can create controlled regeneration tissues for treating numerous organic and tissue lesions. Thus, for example, by removing, under echographic control using a transrectal needle, prostate cells which will be totally or partially cloned and by reinjecting them by the same method into the prostate, this inducing cell rejuvenation could, in certain cases, impede the development of local cancer or decelerate the spreading thereof. Also, a regenerated autologous, or even homologous, ophthalmic retina could be of great benefit in the event of DMLA, and serious renal failure could be combated by implantation of partially dedifferentiated cells obtained, after transfer into and then from oocytes, from nuclei of various nephron cells, and arthrosis could be relieved by the implantation of chondrocytes originating from partial cloning; the same applies to cutaneous surfaces and, in particular, to the regeneration of normal hair, for example by transferring one or more nuclei or parts of nuclei of hair follicle and/or melanocyte cell nuclei into the oocyte, for regenerating hair and/or its colour.

A significant application of the invention is in potentiating or recreating thymus functions by genetic rejuvenation of homologous or, if possible, autologous, partially dedifferentiated thymus cells in order to actively reanimate the immunoprotective functions of the body.

In the event of auricular fibrillation, a main application of the invention involves transplanting these partially dedifferentiated cells which are functionally driven to synchronized contraction in a laboratory by implanting them, for example, in sheets or in grids in contact with the auricular myocardium where they are able to progressively multiply and/or grow and/or genetically modify the diseased cells of the auricular myocardium and/or else also act by secretion and humoral biochemical, mechanical or physical induction activity, perhaps by intervening in a morphogenetic field.

In an advantageous embodiment, a myocardial cell is excised under a microscope, and the membrane and the cytoplasm living in culture after one, more or all of the nuclei have been extracted, are kept. This or these extracted nucleus or nuclei will be introduced individually or in a group into one or more preferably previously enucleated oocytes, and only the pro, meta, ana or telophase will be awaited, preferably by observation under a microscope, before removing them and reintroducing them into the membrane, and the conserved cytoplasm which is living or capable of living in culture or in another myocardial syncytial cell, preferably emptied of some or all of its nuclei.

These cells with more or less dedifferentiated nuclei will be placed in appropriate culture and multiplied, preferably on biodegradable resilient stents, for example a collagen matrix or a resilient fabric which is biodegradable in vivo, and will be stimulated, preferably progressively, by a simple or inotropic orthorhythmic pacemaker in order to adapt physiologically to their future insertion, either in the patient's diseased or senile myocardium, or to constitute the self-contracting walls of a partial or total artificial heart, and will subsequently be implanted in the patient, in particular also in the auricular region so as to suppress auricular fibrillation, in particular also to form segments of active contractile coronary arteries that can be used as physiological conducting and propelling coronary stents, this complementary coronary contractility and active and passive distensibility being able to be induced as required by electrical arterial stimulation of the arterial smooth muscle offset in a diastole relative to the ventricular contraction or to form an almost complete or supplementary coronary artery, for example being able to originate from partial differentiation or cloning of autologous muscle arterial cells and also coronary endothelial cells reconstituting a functional rejuvenated autologous coronary artery optionally on resorbable or other resilient or extensible stents.

In a variation of the invention, a selected portion of a chromosome or a complete chromosome or gene is introduced into a suitable functional oocyte, either individually or accompanied by a portion of the nucleus or of the differentiated cell nucleus, which are preferably original or non-original autologous, partial or complete, to be treated. These nuclei to be treated can be selectively depleted in the disease chromosome or chromosomes which are to be replaced so that the nucleus will tolerate its selective and/or partial dedifferentiation genetic chromosome reconstitution.

A gene or a group of genes may obviously be substituted for the portion of chromosomes or for all the chromosomes to be dedifferentiated without departing from the scope of the invention.

One or more groups of genes can thus be transplanted into a suitable oocyte in the presence or absence of a selected assembly of chromosomes or of at least one cell nucleus of which the selective and partial dedifferentiation, for example during the metaphase or anaphase, will allow precise monitoring by remote optical microscope observation, the chromosomal reorganization for the preparation of the cell division allowing the isolation of the chromosomes and the selective destruction of one or more chromosomes or chromosomal regions, for example by laser radiation in a manner known per se and their replacement by one or more healthy chromosomes or corresponding regions and will then allow the thus modified nucleus to be subjected to partial dedifferentiation in an oocyte.

The partially dedifferentiated nuclei or chromosomes could be extracted, for example, by intra-oocyte injection of a suitable serum under slight pressure after having sufficiently mobilized the nuclear material with a micro-rod or paddle or by vibratory ultrasound or laser action.

A check can easily be carried out by the degree of nuclear or perinuclear integration, this integration being optically visible.

In the case of the creation of complete or partial artificial or artificially induced chromosomes or genes, these elements should often be subjected to partial dedifferentiation of this type in order to create for them a history of genetic development without which their future could be compromised. If these artificial elements with genetic function do not tolerate genetic dedifferentiation involution, their future functionality is uncertain.

Tissue grafts require, for their success, the adequate elimination of serious rejection lymphocyte reactions which are generally of the antigenic, antibody and humoral type in the recipient organism, as observed in pregnant women who biologically tolerate their fetus through their placenta. For example, these characteristics of tolerance, in particular lymphocyte tolerance and the functions of the thymus are to be genetically and/or plasmatically imitated, for example. In adult and, in particular, aged humans, the presence of the thymus cells and functions is often too weak or event absent. It may be beneficial, for example, to transplant a homologous thymus tissue which is partially and selectively dedifferentiated and genetically adapted, for example, by selective chromosomal integration of chromosomes of the graft in cell nuclei of the receiving organism, either by genetic preparation of blood stem cells of the receiving organism or by preparation in in vitro or in vivo cell culture (such as sub- or intradermal) with or without hyperexpression of their telomerase or protein Sir2 in order to prolong their life and bring about their induced habituation to the critical antigen and antibody of the cells to be grafted by the known means of the influence which is induced remotely by biochemical and hormonal substances on the expressions of specific genes.

Cells of this type which are genetically adapted to various receiving tissues can be used, in particular, for the radical cure of auricular fibrillation and for retinal regeneration, implantation of pancreatic tissue without protective membrane, of regeneration nephrons, of intercerebral dopaminergic cells against Parkinson's disease, of dermal and epidermal regeneration tissues, including hair, of prostate or mammary gland tissues for curing the corresponding cancers and, in particular, regenerating thymus cells and any other cells which function in a beneficial or indispensable manner, in particular the digestive, nervous, dermal, respiratory, skeletal and cardiovascular ducts and systems.

Coronary, carotid, renal, etc. arterial lesions may be fatal and ideally necessitate radical tissue and function regeneration treatment. For this purpose, the invention comprises a variation which is capable of removing autologous or homologous arterial muscle cells and subjecting them to controlled partial dedifferentiation by the above-mentioned methods. These arterial cells can then be cultivated either in vitro around a preferably resilient, dissolvable or non-dissolvable stent in the form of a tube and in a serum circulating within a tube under pulsatile pressure which progressively increases so as to recreate the contractile and elastic relaxation function of the cells in order to reconstitute an arterial tube of the desired diameter. Partially dedifferentiated arterial endothelial cells will similarly be cultivated in the form of a smaller diameter tube which will finally be introduced into the largest tube cultivated in this way. Partially dedifferentiated arterial segments of this type which are tolerated by the organism could then either replace diseased arterial segments or be implanted alongside or instead of a defective network.

On the scale of coronary arteries, living auto-contractile "stents" for example which can be implanted, for example by endoarterial catheterization, can thus be created. Current stents are made of an inert immobile plastic or metal material and replace a more or less auto-contractile but thrombosed arterial segment, contributing to the depopulation of downstream small arteries and coronary capillaries. These artificial stents not only lack active action such as coordinated blood propulsion with the local motor arterial wave, but also disturb the dynamics of the normal blood flow of all of the artery concerned, often leading to depopulation of the small vessels downstream of the stents.

On the other hand, as a living autologous reconstituted physiological coronary artery segment which is actively pulsating while potentiating the arterial shower and is if necessary genetically "rejuvenated" by partial dedifferentiation does not cause rejection reactions by the organism receiving the graft, it can reconstitute a very active physiological arterial segment which may additionally be capable of improving blood circulation of the entire artery, for example owing to its mechanical capacity (calling upon the mechanical sensitivity of specific genetic expressions) and owing to genetic secretions and induction of factors capable of remotely inducing a specific cell rejuvenation.

Normally, this "pulsatile physiological stent" will be activated spontaneously, in particular by the variations in parietal and blood pressures. If necessary, the coordinated rhythmic activity of this segment of "physiological stent" can be assured by an arterial electronic pacemaker adapted to the rhythm of the arterial beat, for example by a detector of ventricular or intramyocardial intracavitary pressures and/or the ECG and stimulating during the diastole, for example also relative to the rhythm of the cardiac pacemaker.

A sensor of pressures, of the oxygen saturation and of the ECG can also be placed on such an arterial stent, preferably toward its distal end, during in vitro tissue reconstruction, these sensors thus being totally surrounded by living tissue, and can connect the output wires, preferably to the cardiac pacemaker or implanted defibrillator so that the effective local blood circulation will be known continuously, without carrying out instantaneous radioscopy with injection of contrast substance.

In order to maintain the requirements of an emergency operation for positioning a conventional stent, an immobile stent which is progressively dissolvable or removable or infiltrable by the "physiological coronary reactivation stent" should be implanted urgently by catheterization.

In a preferred variation of the invention, this reconstituted coronary arterial segment is provided, in living continuity, with arteries, arterioles, capillary and venous networks with their irrigated myocardial tissues; this functional tissue block being previously cultivated and multiplied in vitro or in vivo, preferably from autologous, partially dedifferentiated cells, an adequate venous join of this tissue being provided toward the ventricular cavity or the coronary venous sinus. This highly functional renovated myocardial unit can progressively induce recolonization of the capillaries and small coronary arteries of the original myocardium.

The implantation of a physiological stent by conventional arterial catheterization will initially operate by imbibition of arterial blood supply, as performed during the culturing thereof, from the endoartery.

The high vitality of the renewed physiological stent will progressively create new vaso-vasorum. The dominant vitality of this arterial segment will subsequently produce a degree of widening of the caliber of this stent as a function of its metabolic requirements.

An additional application of the invention involves progressively reconstituting in vitro preferably after partial dedifferentiation of the initial cells of various cardiac tissues and the incipient multiplication thereof, a portion of ventricle, for example in the case of ventricular aneurysm or necrosis or all of two ventricles, using extensible or fairly flexible or biodegradable carriers and suitable growth factors and while respecting the ventricular geometry in three dimensions so as to produce vascular connections of the type which can be obtained from echocardiography in three dimensions (N. Mirochnik, A. Hagège, F. Zacouto and C. Guérot: Arch. Mal. Coeur, Paris, 93, Oct. 10, 2000).

In other variations, the invention can be applied to cell and tissue grafts without serious rejection reactions by the use of partial and/or selective cloning.

In a variation of the invention, a selected portion of a chromosome or a complete chromosome is introduced into a suitable functional oocyte either individually or accompanied by one or two preferably autologous partial or complete cell nuclei from the recipient or non-original to be treated. These nuclei to be treated can be selectively depleted of one or more diseased chromosomes, in particular which can be isolated during a phase of their mitosis, which are to be replaced by equivalent chromosomes preferably of the embryonic or genetically partially dedifferentiated type so that the nucleus will tolerate its selective and/or partial dedifferentiation genetic chromosome reconstitution.

One or a group of genes can obviously be substituted for the portion of chromosomes or complete chromosomes to be dedifferentiated without departing from the scope of the invention.

One or a group of genes can thus be transplanted into a suitable oocyte in the presence or absence of a selected assembly of chromosomes or of at least one cell nucleus of which the selective and partial dedifferentiation, for example during the metaphase or the anaphase, will allow, by remote optical microscope observation, precise monitoring of the chromosomal reorganizations in preparation for cell division by means of movements and appearances of the intracell elements or centriolar nuclear elements, the beginning of formation of a nuclear membrane, movements and densification of chromosomes, etc. In other words, groups of genes or selected chromosomes should be sufficiently dedifferentiated beforehand and then transplanted into a nucleus-carrying oocyte which should be genetically modified and previously deprived of the diseased chromosome or chromosomes concerned.

A variation of the invention consists in partially co-dedifferentiating in a same or autologous denucleated oocyte to induce reciprocal immune tolerance between, on the one hand, a cell nucleus of which one or more diseased or senile chromosomes or parts of chromosomes have been destroyed during the mitosis thereof and, on the other hand, one or more healthy portions of chromosomes or complete chromosomes, preferably homologous, healthy younger chromosomes. Cells of this type which have been genetically repaired and dedifferentiated can also receive an over-expression of their telomerase or Sir2 protein.

The partially dedifferentiated nuclei or chromosomes could be extracted, for example, by intra-oocyte injection of a suitable serum under slight pressure, after having sufficiently mobilized the nuclear material with a micro-rod or paddle and/or the application of local vibratory ultrasound or laser action.

The degree of nuclear or perinuclear integration could easily be checked, this integration being optically visible.

In the case of the creation of complete or partial artificial or artificially induced or disposed chromosomes or genes, these elements should often be subjected to partial dedifferentiation of this type in order to create for them a history of genetic development without which their future could be compromised. If these artificial or artificially combined elements with genetic function do not tolerate a history with targeted genetic dedifferentiation, their future functionality is uncertain.

A practical example of the process can be to acquire the hemodynamics and optionally the corresponding oxygen consumption and then to determine the intervals of couplings of the paired stimulation relative to the R wave of the ECG in ms or relative to the R-R interval as a percentage of the duration of the earlier cycle, or by an algorithmic combination of the two. A pulse train is transmitted for at least one cycle. The hemodynamics for one cycle are acquired and are compared with the spontaneous hemodynamics while checking that the increase obtained exceeds a programmed percentage, for example 20%. If the desired values of hemodynamics and optionally of oxygen consumption are attained, this OIST is continued and the acquisition of the hemodynamics and preferably of the myocardial oxygen consumption is continued. If the programmed values are not attained, at least a parameter of the pulse trains is modified and the checks are repeated. If the desired values are not obtained after the successive programmed changes of the parameters of the pulse trains, the OIST is stopped.

Figure 5:
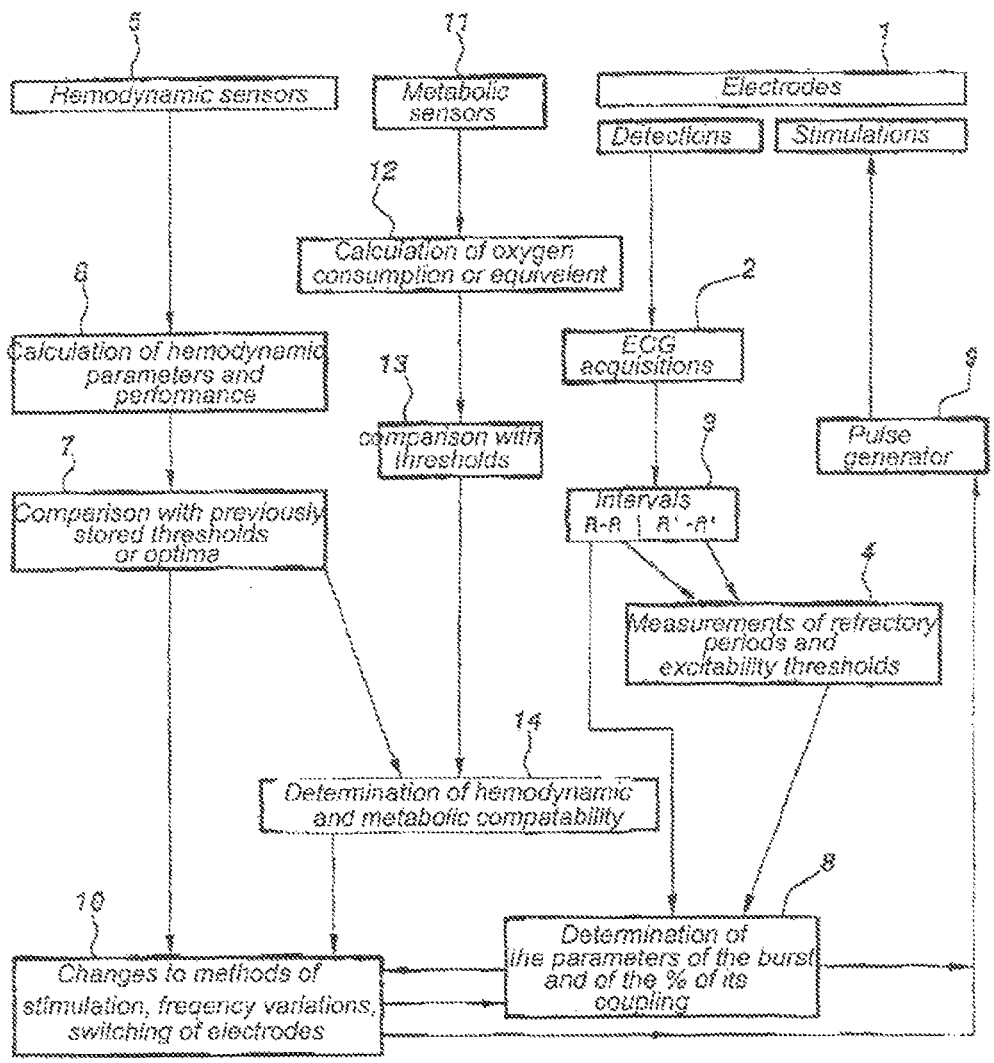
FIG. 5 is a block diagram of a device according to the invention.

FIG. 5 shows, by way of example, a block diagram of an implanted device according to the invention.

The technical embodiment of the various hardware or software components will not be described in greater detail, whether they be the detection or stimulation means, the energy sources and the auto processing and memory means, as they are all quite conventional and well known in implanted stimulators nowadays.

The device comprises electrical detection and stimulation means 1. For example, detection electrodes which can also be used for stimulation, as is often the case. Detection means supply the acquisition means of the electrocardiogram 2 with signals. These acquisition means allow, in particular, the heart rhythm, namely the RR intervals of the muscle contraction generating waves and R—R', in other words the interval between the wave R and a coupled wave R' induced in accordance with the invention at the end of the refractory period to be obtained and stored in the logic means 3 (K. Theisen, F. Zacouto, M Grohmann, H. Jahrmärker: Refraktärzeitmessung bei absoluter Arrythmie mit orthorythmischer Serienstimulation, Klin. Wochenschr., 52, 1082-1084 (1974) Springer-Verlag). These means also allow determination of the pulses of the pulse burst which caused the wave R'.

It is thus possible to obtain the determination of the refractory period at 4.

The device also comprises hemodynamics detection means 5 such as an intracardiac or intramyocardiac pressure sensor and impedance measuring volume sensors, and means measuring the kinetic energy of each expelled volume (for example by measuring the gradient $\Delta p/\Delta t$ of the pressure and/or volume variations, or again by Doppler effect implanted sensors or accelerometers, these means allowing, in the means 6, the acquisition of this data for calculation of the hemodynamic performance, in other words of the ejected blood volume and, by relating it to the rhythm, of the heart rhythm. Preferably, the hemodynamic sensors 5 comprise an intramyocardial pressure sensor situated close to an intraventricular detection and stimulation electrode belonging to the means 1. The means 6 are sensitive to the pressure amplitude detected by the pressure sensor and check whether this amplitude varies just after the rise in pressure, so as to determine the zone MMRZ. The values originating from the means 6 are sent to comparison means 7 in which there is also stored either a threshold above which the hemodynamics are to be maintained or a hemodynamic optimum which will have been recorded, for example beforehand, by the device according to the invention. These means 7 send the result of their calculation to means 8 which also receive information relating to the refractory period originating from the means 4 and to the characteristics of the electrocardiogram, in particular the rhythm originating from the means 3. The coupling, in other words the interval provided between the last wave R which has just been detected and the transmission of the stimulation or of the stimulating burst of pulses, is determined in the logic means 8. These means can also modify not only the coupling interval, if necessary, but also other characteristics such as the duration of the burst, the number of pulses, the pulse interval or else the intensity or duration of each of the pulses, as a function of the information received.

The means 8 control the means 9 for generating a burst of pulses.

The means for comparison 7 as a function of the degree of efficacy of the observed hemodynamics and its comparison with the desired values can also optionally modify the frequency of the stimulations by means 10 which control the pulse generator 9, for example in particular when the spontaneous electrogenesis of the patient is inadequate to cause a suitable heart rhythm.

The device can also comprise metabolic sensors 11, for example sensors of local oxygen saturation pressure or of its equivalent in concentration of transmembrane or free electrons as measurable by an oxydo-reduction co-efficient within a vein of the coronary sinus and, for example, relating to the right intra-auricular venous blood and the left intra-auricular arterial blood and/or $CO_2$ and/or pH etc. sensors connected to acquisition means 12 determining a value such as the $O_2$ consumption acquired for a comparison in means 13 with one or more programmed or previously stored thresholds. A logic means 14 which influences the means 10 (or in a simpler case, the means 8) can thus be employed in order to modify, if necessary, the parameters or the coupling of the burst or other variations provided in the means 10.

Figure 6:
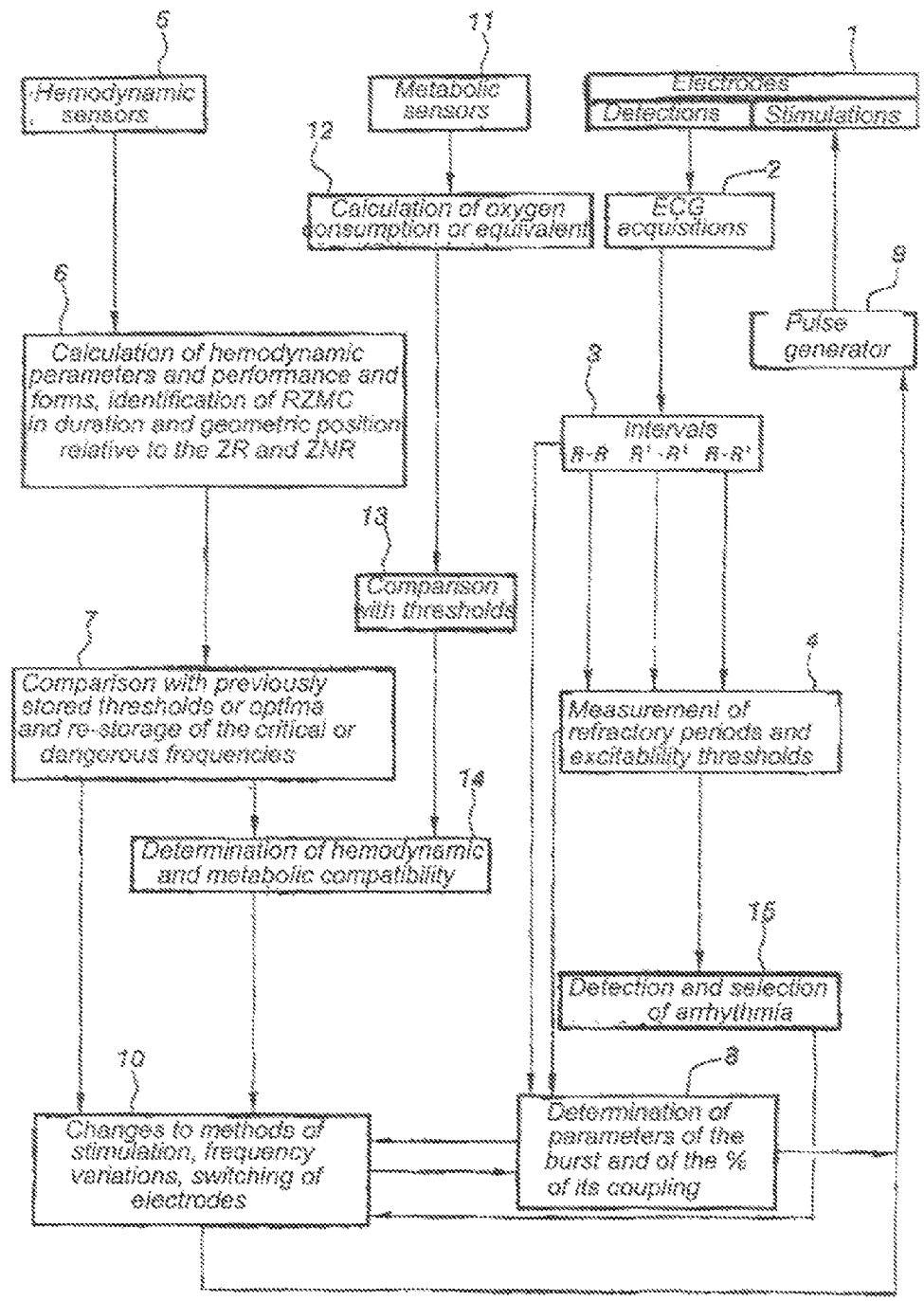
FIG. 6 is a schematic view of a device according to FIG. 5, also having additional features.

The device in FIG. 6 has means identical to that described in FIG. 5 and additional features. The means 6 is thus arranged so as to be able to identify the zones MMRZ in duration and geometric position relative to the zones RZ and RNZ.

The means for comparison with already stored optimum series can be arranged so as to store dangerous critical sequences which have already existed or have been entered by programming and allow an action if a sequence of cycles which is considered to be critical is detected in order, for example, to act on a defibrillation means or to stop operation of the device according to the invention and to cause it to operate in the manner of a conventional orthorhythmic pacemaker or VVI or DDD.

The means 3 is also arranged so as to also acquire the intervals R—R' directly.

Finally, an additional means 15 is provided to receive information from the means 4, these means 4 being arranged so as to acquire information also on the arrhythmias, said means 15 thus allowing the detection and selection of arrhythmias, preferably the distinction between spontaneous arrhythmias and those induced by the device, said means 15 retroacting on the means 10 which controls the transmission of the pulses.

During echocardiography, the OIST at rest allows a basal CC to be immediately followed by one or more CC with maximum contractility or vice versa and enables their quantitative and geometric difference to be measured. For a progressive effort test, however, it would be necessary to use conventional means. The comparison between maximum contractility of the OIST and that obtained by physical effort or substances of the dopamine, noradrenaline, etc. type could give new indications of myocardial function.

The automatic measurement of the variations of the refractory zones ERZ and MRZ during the effort tests, in particular under echocardiographic control, provides information on an intracellular myocardial state.

In the case of functional resynchronizing bi-ventricular cardiac stimulation used, for example, in the case of a blockage of the left branch, grave hypertrophy of the myocardium etc., the hemodynamic result can basically be further improved by adding a OIST which is controlled by the bi-ventricular stimulator which will reinforce the intrinsic contractility of each ventricle and lead to genetic regeneration which will be observed in the region of the myocardiums subjected to prolonged intensive physical training with peripheral muscle exercises.

Figure 3:
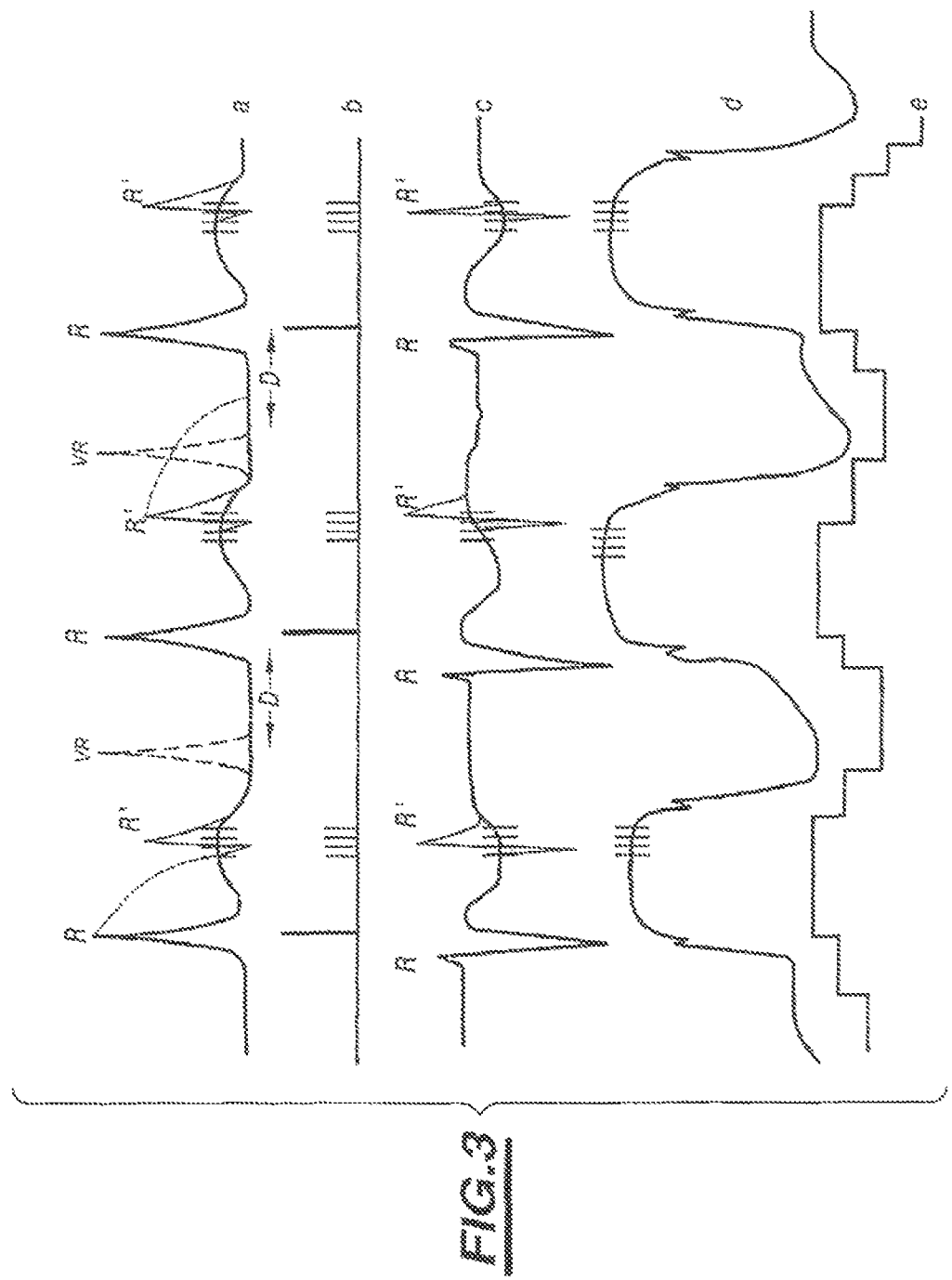
FIG. 3 shows the acquisition of various parameters during operation of the device.

An automatic OIST according to the invention comprises a device for assuring optimum hemodynamics within adjustable limits, for example of rhythm, pressures: max., min., differential, of dimensional variations of the contraction, local and general oxygen saturations (preferably in the coronary sinus and the arterial and venous blood), of regular continuity of the OIST, etc. In order to be able to carry out this development, a specially programmed display should be provided, for example (FIG. 3) in the region of an oscilloscope having a plurality of simultaneous channels and while using known signal processing and algorithms, which comprises, for example, the following parameters in real time:

an ECG curve showing 3 to 5 cycles with rapid development, the marking of spots (spikes) for detections and stimulations in the region of the electrodes on a line, a curve showing the preferably monopolar intracardial ECG, for example on a tripolar probe, stimulation being carried out in bipolar mode which allows the pulse of a burst which effectively caused the propagated electrical depolarization to be determined thus allowing the automatic measurement of the ERZs and the variations thereof during each CC, these measurements being made possible by the orthorhythmic pacemaker, even in the cause of auricular fibrillation (K. Theissen, F. Zacouto, Klin. Wschr. 52, 1082-1048, 1974, Germany, Springer-Verlag), a curve showing the mechanical curves, variations in pressures, volumes and acceleration, a curve showing the consumption of oxygen or an equivalent if possible for each or a few cycles such as, for example, venous and arterial coronary oxygen saturations and their difference and/or a local arterio-venous oxydo-reduction co-efficient, etc., which can preventively alert, prior to hypoxia, of any over-consumption of oxygen by the myocardium which is manifested, for example, firstly by an extra membrane accumulation of electrons.

The OIST stimulating device can be combined with all categories of implantable automatic cardiac stimulators AID, and also, in particular, automatic anti-tachycardic defibrillators, VVI, DDD, DDDR, etc.

Figure 7:
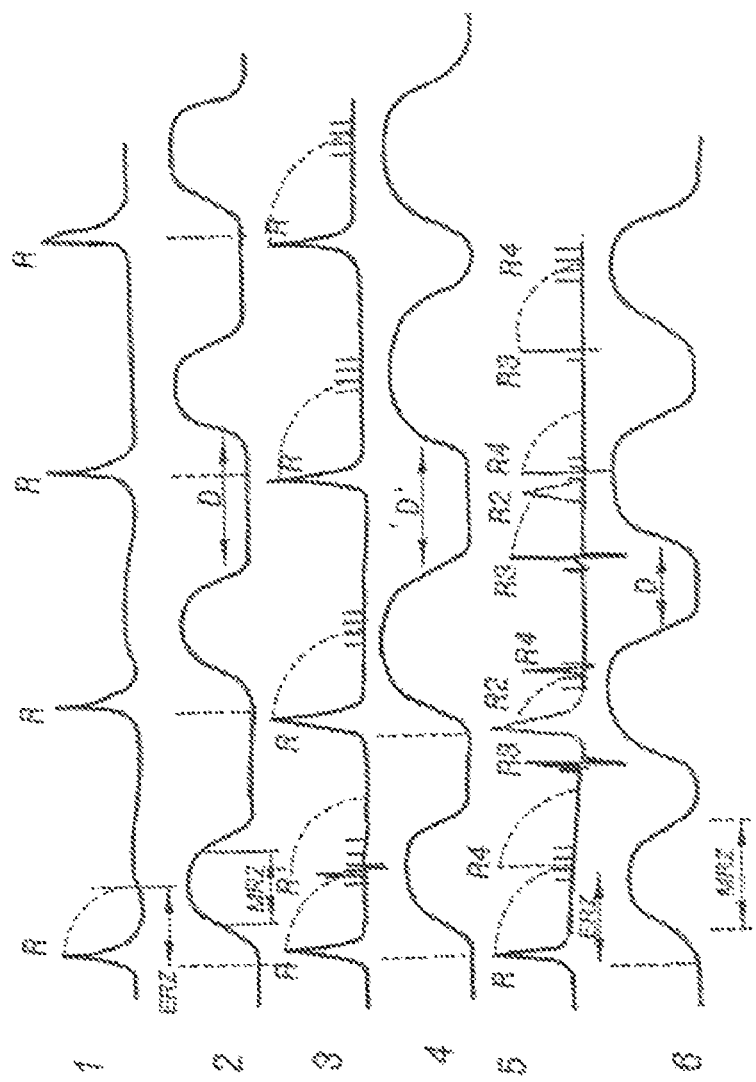
FIG. 7 shows schematically the electrocardiogram and mechanogram of an OIST according to the invention for a slow spontaneous rhythm.
Figure 8:
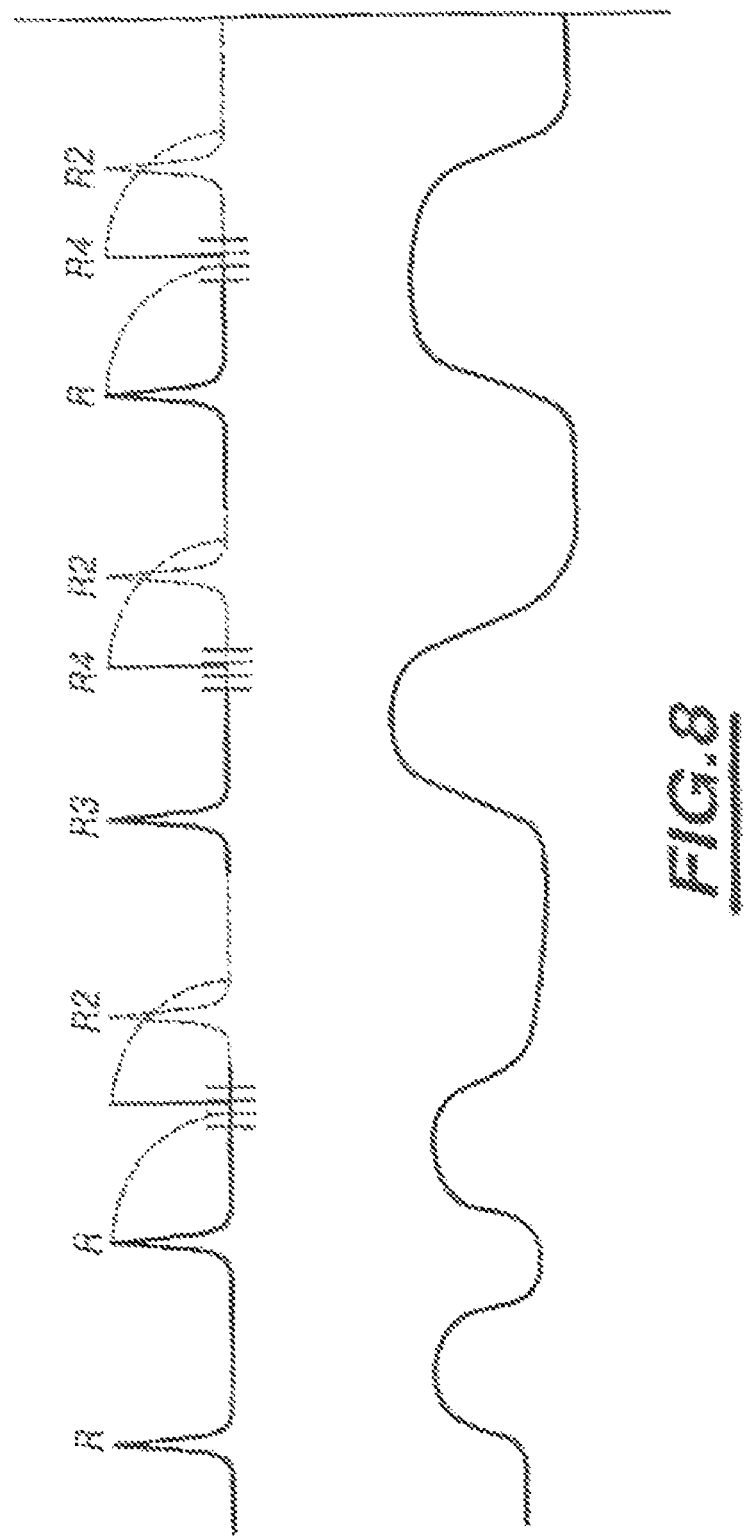
FIG. 8 shows schematically the electrocardiogram and mechanogram of a bradycardizing OIST.
Figure 9:
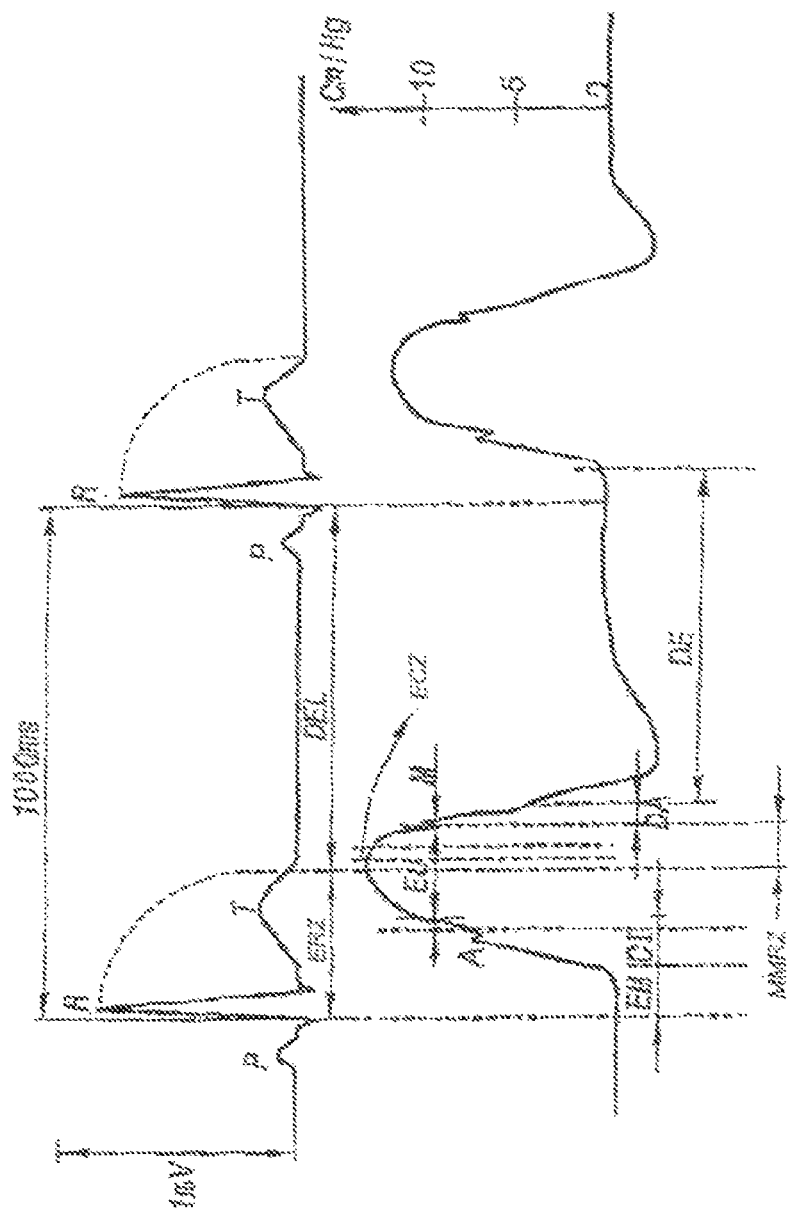
FIG. 9 shows schematically the various electrical and mechanical zones distinguished in the invention.

Reference will be made to FIG. 7 to 9 by way of example.

In this example, the practitioner or the device according to the invention notes that a patient suffering from a massive heart failure has a non-accelerated spontaneous heart rhythm, for example of less than 125 p/min and, for example, preferably less than 100 p/min.

Line 1 in FIG. 7 shows the regular rhythm of the waves R (of the complexes QRS) of this patient, ERZ representing the electrical refractory zone determined, for example, by one of the means described in the present invention.

Line 2 shows the mechanogram detected in response. The mechanical refractory period MRZ as well as the mechanical diastole D has also been shown on this curve.

The electrocardiographic simulation of isotropic stimulation according to the invention, in which a coupled burst is transmitted immediately at the instant of the end of the electrical refractory zone ERZ is shown on line 3, and the extension of the refractory zone following the complex R' induced by the simultaneous coupled stimulation can be seen. In this simulation, the data processing means of the device have anticipated that the base rhythm is barely modified by simulated inotropic stimulation and the spontaneous complexes R therefore occur as they did in the absence of stimulation.

Line 4 shows the estimated increase, in duration and intensity of the mechanogram, the increase being immediately observed as from the second spontaneous wave R, in other words the first to follow inotropic stimulation R'.

A reduction in the mechanical diastolic duration D', which is less than D also results.

The actual inotropic stimulation of the heart is thus carried out as provided on the simulation curve 2 in FIG. 7, and it is checked that an increase in hemodynamic performance is obtained immediately after the successive first cycle, as in line 4. This check is continued for a specific duration or a specific number of cardiac cycles, for example corresponding to one or a plurality of tens or about one hundred cycles, bearing in mind that a progressive supplementary increase extending over tens or hundreds of successive cycles should normally be obtained after the immediate increase in performance during the second cycle.

The effect obtained by inotropic stimulation according to the invention can also be simulated in the same patient on the basis of the fasted rhythm imposed by the stimulating pulses R3 which prevent the occurrence of the spontaneous signals R (the suppressed complexes QRS are represented by R2). The line 5 shows the electrocardiogram corresponding to this simulation with coupling of bursts and electrical capturing of the heart.

The line 6 represents the estimated increase in the mechanogram owing to this simulation. Owing to the comparison means of the device, the effects of the stimulations in lines 2 and 6 can thus be compared and, for example, in the case where it would be estimated that the increase in hemodynamic performance originating from a mere coupled stimulation according to line 3 is inadequate, the implementation of a stimulation according to line 5 could be proposed if the increase and the desired mode is greater and allows an acceptable increase in cardiac performance to be obtained, for example a doubling relative to the spontaneous heart rhythm as estimated in line 2.

Once the choice of simulation has been made, the device effectively proceeds with inotroptic stimulation according to line 3, as described hereinbefore or according to line 5 as a function of the choice made, and the means for acquisition of the hemodynamics and/or the oxygen consumption thus allow the existence and extent of the increase in hemodynamic performance to be checked and compared with the simulated increase.

In the absence of the increase in the hemodynamic performance, for example during the two first coupled or paired stimulating cycles, the device stops inotropic stimulation.

On the other hand, if a hemodynamic increase is observed, stimulation is continued, preferably over several tens or one or more hundreds of cycles. The hemodynamic performance obtained is thus compared with this result of simulation. If the performance obtained is comparable to the target performance, for example in a range of 15% of the target performance, inotroptic stimulation is continued. If the increase in performance obtained greatly exceeds the simulated increase, the device can optionally reduce the performance, for example by allowing for a cardiac stress index CSI and comparing the performance index CPI and stress index CSI, as described in the U.S. Pat. No. 5,213,098 incorporated here by reference, and the inotropic simulation can optionally be performed only for a reduced proportion of cycles. On the other hand, the observed performance is far less than that estimated to be necessary and anticipated by the simulation, the device can stop inotropic simulation.

Referring to FIG. 8 there is shown a case of cardiac failure associated with a spontaneous tachycardial rhythm, for example greater than 125 cycles per minute. The last spontaneous cycle R is shown together with the corresponding hemodynamic performance in line 2.

In such a case, the device simulates the transmission of a stimulating burst toward the end of the refractory period of the last spontaneous signal R and this extends the refractory period of the heart so that the following complex QRS which will be produced at instant R2 owing to the tachycardia can no longer be produced and this causes the occurrence of a retarded spontaneous complex R3. The coupling stimulating burst R4 is thus continued and it can be seen that by preventing the occurrence of the spontaneous tachycardic complex R2 each time, a lower rhythm, for example divided by two, is finally obtained.

Usually however, it is preferable to carry out complete electrical management of the heart; the spontaneous complex R3 is thus replaced by stimulation at a slightly faster rhythm.

Increased simulated hemodynamic performance normally corresponds to this stabilized normal rhythm because the EPR (PESP) effect largely over-compensates the reduction in the number of contractions per minute.

If this simulation promises adequate hemodynamic performance, inotropic stimulation according to the procedure in line 1 of FIG. 8 is actually carried out and, as mentioned hereinbefore, the response and amplitude of the response obtained is checked for one, two or three cycles then for a greater number of cycles. In such an embodiment, a stimulating pulse can be transmitted at a higher rhythm if the simulated or actually obtained hemodynamic performance is inadequate.

FIG. 9 shows the electrocardiogram and the corresponding mechanogram of a patient. The electrocardiogram shown is line 1 shows the complexes QRS and, more precisely, the wave R which is spontaneous or stimulated at a base rhythm, for example of 60 pulsations/min. The appearance of the complex QRS creates an electrical refractory zone ERZ which ends more or less with the wave T without an adequate correlation generally being able to be established. This refractory zone is followed by the electrically sensitive diastole ELD.

Line 2 shows that the increase in pressure of the mechanogram takes place after an electromechanical coupling period EM, hereinafter also called E. An isovolumetric contraction first occurs when the valves are not open, for period CI. This contraction is followed a contraction with blood ejection EJ between the opening A of the aortic valve and the opening M of the mitral valve. DE represents the mechanical diastole, which is firstly a motor diastole and then elastic and passive for filling.

The maximum mechanical refractory zone during which the cardiac muscle is in the most contracted state is represented by MMRZ. This zone, which corresponds to the peak of the pressure curve is relatively flattened in the illustrated example because the pressure curve has been obtained by a sensor which measures the intracavitary blood pressure within the ventricle. When an intramyocardial pressure sensor is placed in a local region or zone, however, the rise in local pressure is very pronounced and allows the local maximum mechanical refractory zone close to the active electrode to be distinguished easily.

In an embodiment of the present invention, the electrocardiogram of line 1 is acquired in this local region, for example preferably the myocardial region adjacent to the ventricular stimulation and detection electrode, and the intramyocardial pressure is also acquired in this myocardial region. It is reasoned hereinafter as if the curves of lines 1 and 2 in FIG. 9 represented local curves in the selected region.

It is thus observed that the electrical refractory zone can partially or even completely overlap the zone MMRZ. If the superimposition is partial, an effective critical zone ECZ to be targeted, which may be equal to the zone MMR if the electrical refractory zone ERZ ends before the beginning of the zone MMRZ and may be zero is ERZ is elongated and encompasses the duration of the zone MMRZ is defined between the zone ERZ and the end of the zone MMRZ.

According to a particularly preferred embodiment of the invention, the coupled or paired stimulation is transmitted during the zone ECZ. This may quite frequently be approximately 30 to 40 ms and, in this case, the sufficiently early transmission toward the end of ERZ of a burst of pulses having a pulse interval, for example of 20 ms, will certainly cause a stimulation in the targeted zone ECZ without a detrimental increase in the local oxygen consumption, this stimulation producing the post-extrasystolic potentiation expected with the slightest increase in oxygen consumption relative to the increase in mechanical work by the myocardium PESP.

If the zone ECZ tends to shrink, the device could thus advantageously reduce the interval between the pulses of the burst so as to guarantee that a pulse of the burst will fall in this zone ECZ. However, it is preferable not to shrink the duration between two successive pulses substantially below 10 ms, the electronic means not allowing the stimulating pulse of the burst to be identified in this case.

Consequently, if the zone ECZ is less than 10 or 15 ms, it is preferable not to transmit paired or coupled pulses.

The same applies if it observed over a specific number of cycles that the zone ECZ varies too anarchically in duration or time.

In a particularly advantageous embodiment, the zone ERZ will be detected by using pulse trains as described hereinbefore, and the positions and durations of the zones ECZ of a plurality of cycles, for example from 30 to 3000 cycles, will be stored for detecting whether the zone ECZ is almost stable or whether it has a tendency to decrease or increase and an intervention could thus be made, this time by transmitting a stimulating pulse, preferably rather toward the estimated end of the zone MMRZ of the current cycle, assuming that the zone ECZ exists at this instant.

Owing to this storage and checking which could be carried out by the analyzing simulator ASIM according to the invention, it could be brought about that only a small number and even no pulse causing electrical depolarization occurs outside the zone MMRZ, thus allowing the local oxygen consumption caused by the inotropic paired or coupled stimulation to be limited. By suitably selecting the place in the heart where the intramyocardial pressure and the electrical depolarization are detected and by stimulating in or in the vicinity of this location, the intramyocardial propagation of the depolarization, caused by the inotropic stimulation, could be made to take place in concordance with the continuous propagation of a strong contraction, in particular a maximum myocardial contraction in the new territories where stimulation depolarization is propagated, so that the oxygen consumption resulting from the paired or coupled stimulation will also remain limited in a large portion or even all of the ventricular myocardium. For this purpose, it is preferable to detect the zone MMRZ in an initial myocardial zone where the propagation of depolarization begins, the electrical influx thus being propagated in the remainder of the myocardium at the same time and at a speed substantially equal to the maximum contraction, the coupling thereof remaining sufficiently constant.

In certain particular cases, for example if a change in the operation of the intramyocardial bundles of conduction has been detected, for example in the case of pathological blocks of branch or local zones, the zone MMRZ and optionally the corresponding electrical depolarization signals could be detected in a plurality of locations and stimulated in these locations during their respective zones MMRZ or more precisely ECZ.

FIG. 10 shows the increase in the simulated hemodynamic efficacy over three spontaneous cycles in a patient.

Line 1 represents the spontaneous rhythm, for example of 90 p/mm in a patient suffering from acute cardiac failure.

Line 2 shows the spontaneous variation in pressure in the left ventricle generated by the spontaneous rhythm.

Line 3 shows the electrogram of a paired stimulation simulated in this same patient, which maintains a rhythm identical or similar to that in line 1.

Line 4 shows the resultant simulated variation in left intraventricular pressure.

Line 5 consists of a superimposition of the actual pressure differences in line 2 and simulated pressure differences in line 4, the differences being hatched. It can be seen, in particular, that the initial gradient of increase in systemic pressure $\Delta p/\Delta t$ increases by 25% and the diastolic $\Delta p/\Delta t$, in other words of reduction in pressure, by more than 30%.

The flow per systole is increased by 35% and the flow per minute by 33%.

The duration E of electromechanical coupling is reduced by 30%.

The analysis of this simulation shows a significant increase in hemodynamics.

Figure 11:
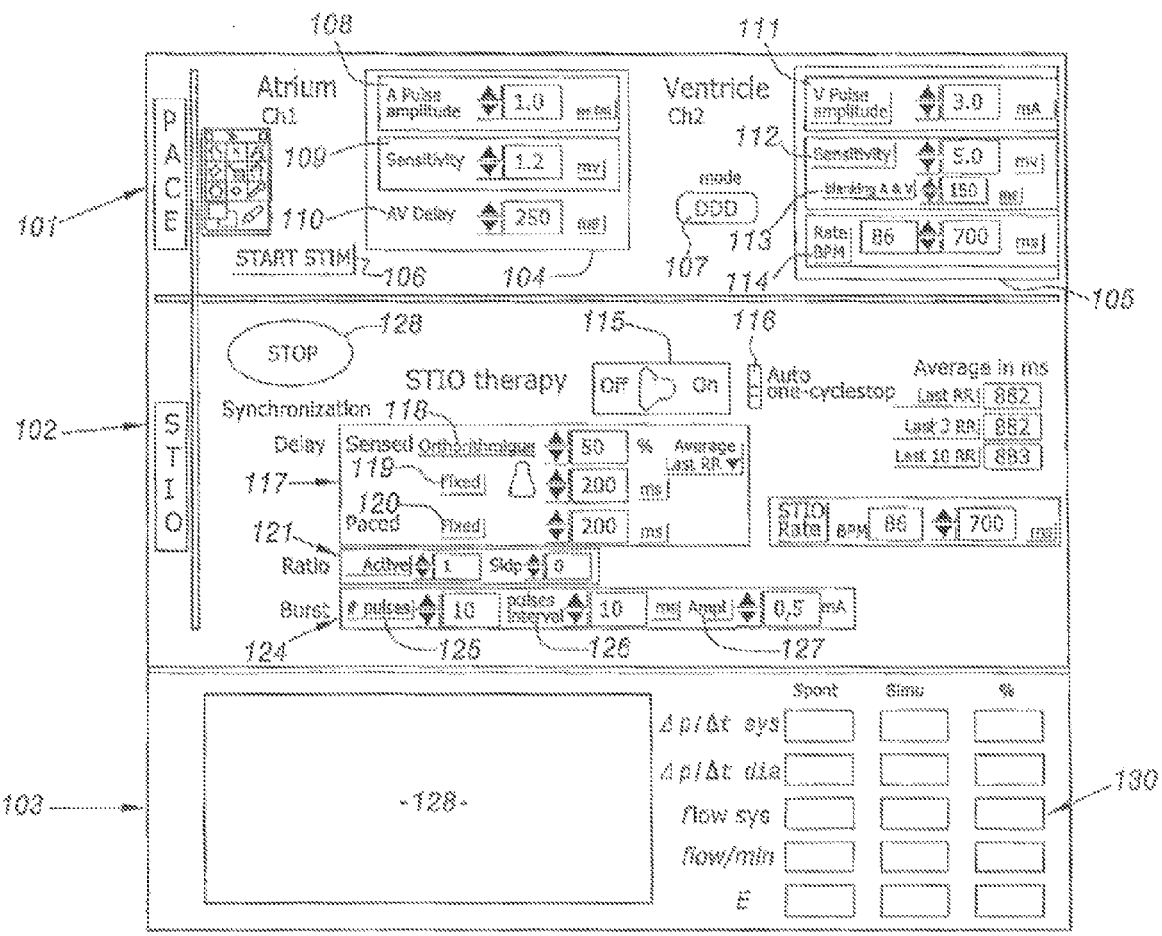
FIG. 11 shows a control and display panel of a device according to the invention.

FIG. 11 shows the control panel of a device ASIM according to the invention, divided into three parts 1001, 102, 103.

The panel 101 comprises a subpanel for auricular control 104 corresponding to the auricular stimulation and detection electrodes and a ventricular subpanel 105 corresponding to ventricular stimulation and detection electrodes. The panel 104 has three control buttons, namely 108 for selecting the amplitude of the stimulating pulses, 109 for the sensitivity of detection and 110 for the duration between the auricular and ventricular stimulations, if the mode DDD is selected. The ventricular panel 105 comprises three buttons 111, 112, 113 for the adjustment and amplitude of the ventricular pulses, the sensitivity of the ventricular detection electrode and the auriculo-ventricular offset. The button 114 allows the orthorhythmic stimulation rhythm to be defined. The button 106 allows the stimulation to be carried out or interrupted and the button 107 allows a passage to auricular, ventricular or DDD mode.

The panel 102 comprises stimulation control buttons OIST according to the invention. The button 115 allows the stimulation OIST to be carried out or interrupted and the button 116 allows automatic stimulation to be triggered only for a single cycle.

The subpanel 117 has a set of buttons, namely 118 for coupling (as a percentage), 119 for coupling in fixed ms, 120 for displaying the base stimulation period.

The subpanel 121 allows the proportion of cycles to be stimulated to be selected.

The subpanel 124 has three buttons 125, 126 and 127 for defining the parameters of the pulses of the burst of inotropic stimulating pulses, namely the number of pulses in the burst by the button 125, the interval between the two successive pulses in the burst by the buttons 126 and the amplitude of the pulse of the burst (button 127).

The emergency stop button 128 allows the immediate stoppage of inotropic stimulation.

The lower portion 103 allows the simulation ASIM according to the invention to be displayed and adjusted and allows the simulation to be compared with the initially detected parameters by optionally actuating the portion 101 and with parameters originating from the actuation of an OIST by the panel 102.

The portion 103 comprises a screen 128 on which the electrical and real and simulated mechanical curves and the juxtaposition thereof appear as shown in FIG. 10.

A subpanel 130 displays the spontaneous values detected (spont), corresponding simulated values (simu) and the comparisons thereof as a percentage of spontaneous value, for the parameters diastolic Δp/Δt, systolic ventricular rate, ventricular rate per minute and electromechanical coupling value E of the ventricle.

EXAMPLES

The following examples are intended as illustrative and not limiting as to various embodiments of the present invention, slight modification and/or addition to these Examples is intended to be expressly covered hereby.

1. Device for stimulating and/or potentiating the heart muscle and/or the myocardial cells, allowing a significant increase in the hemodynamic performance of the heart and/or the treatment of tachycardia, tachyarrhythmia or auricular fibrillation, comprising:
    means for the automatic acquisition (1, 2, 3) of the heart rhythm and optionally of its origin, for detecting, in particular, the interval between at least the last two waves R (induced or spontaneous) of the cardiac cycle just completed,
    means for the precise acquisition of cardiac hemodynamics,
    means (4) for determining, continually or periodically, in real time, the duration of the electrical refractory period (ERZ) following the last wave R of said cycle,
    means for evaluating at least one parameter relating to the functional cell state of the myocardium,
    and means (8, 9, 10) which are subordinate to said evaluating means for sending, substantially without delay at the end of said refractory period (ERZ), at least one paired or coupled stimulating pulse adapted to said functional cell state.
2. Device according to example 1, wherein said evaluating means determine the position and duration of a critical zone effective in targeting ECZ, which is placed immediately after the end of the electrical refractory zone and terminates at the end of a refractory zone of maximum myocardial contraction MMRZ, the transmission of said stimulating pulse intervening in said ECZ zone if it is present and targetable.
3. Device according to either example 1 or example 2, wherein said evaluating means detect the excitability threshold of the myocardium during each cycle or periodically.
4. Device according to any one of examples 1 to 3, wherein the means (8, 9, 10) send a burst of stimulating pulses substantially at the end of said refractory period (ERZ), the duration of the burst and the pulses repetition interval being such that a stimulating pulse of the burst is sent to the heart substantially without delay after the end of said refractory period.
5. Device according to example 4, wherein the means (4) for determining the duration of the electrical refractory period (ERZ) are sensitive without delay to the detection of the pulse of a burst which triggered a complex (R').
6. Device according to any one of examples 1 to 5, wherein, even when the device generates a single stimulating pulse instead of a burst, the means (4) for determining the duration of the refractory zone are arranged so as to acquire, by scanning a second pulse, the substantially exact duration of the refractory zone, this scanning being carried out, for example, during the preceding or current cardiac cycles.
7. Device according to any one of examples 1 to 5, wherein the beginning of the burst of stimulating pulses is selected so as to begin just before the estimated end of the refractory period, and the duration of this burst and consequently the number of stimulating pulses is advantageously such that at least one stimulating pulse will occur before and a following pulse very quickly after the end of said refractory period.
8. Device according to any one of examples 1 to 6 comprising means for advancing or retarding the burst relative to an estimation of the refractory zone and/or modifying the pulse interval within the burst, the device having automatic acquisition means, in particular by obtaining the intracardiac ECG for determining, in particular by processing the intracardiac electrical signal in the region of the detecting and/or stimulating electrode, which stimulating pulse in the burst triggered the wave R' and for functionally modifying the burst.
9. Device according to any one of examples 1 to 8, comprising means which are sensitive to the spontaneous or stimulated waves R and/or to the determination of the electrical and mechanical refractory zones, in particular by scanning all of the burst or only within this burst and/or means for the very rapid determination of the heart excitability thresholds, for example by providing stimulating pulses of variable intensity, including subliminal pulses for allowing the instantaneous measurement thereof within the burst.
10. Device according to any one of examples 1 to 9 comprising anti-tachycardic stimulation means and extrasystole-sensitive means for automatically stopping said stimulation on occurrence of excessively great hemodynamic instability and electrical arrhythmia corresponding to predetermined criteria.
11. Device according either example 9 or example 10, comprising, in addition to the rhythm acquisition means, refractory zone duration determination means and single pulse or burst transmission means, means (7, 10) which are sensitive to the precise acquisition of the hemodynamics relative to the rhythm and its origin in the heart for determining variations in hemodynamic efficacy, these means being capable of controlling the transmission and optionally the parameters of the pulse or the burst, preferably at a rhythm close to that which produced the most favorable hemodynamics for the patient at a given moment.

12. Device according to example 11, wherein said means act on parameters such as: a programmed ventricular rhythm and/or an automatic adjustment of the beginning or end or duration of the burst or the number or the characteristics, in particular width, interval intensity, polarity of the pulses in the burst, or else a location of the transmission of the burst at one or more stimulating electrodes.

13. Device according to example 12, comprising means for progressively reducing a burst to a single pulse or a small number of pulses, in particular by periodically probing with at least a second pulse which moves progressively ahead of the stimulating pulse to automatically measure the beginning of the non-refractory zone so that, when the exploratory pulse retracts towards the stimulating pulse, the stimulating pulse can be retarded, in particular periodically in the event of instability in operation until the beginning of the reduction of the ventricular pressure/volume curve or increase in the oxygen consumption and/or a corresponding parameter, in particular the membrane secretion of electrons, local pH or ketone bodies is obtained, this position corresponding to the exceeding of the end of the maximum contraction mechanical refractory zone (MMRZ)

14. Device according to any one of examples 1 to 13 further comprising means (11, 12) for acquiring metabolic parameters, in particular concerning local oxygen consumption and/or equivalents thereof such as the measurement of the densities of accumulated electrons, lactic acid, pH or ketone bodies.

15. Device according to any one of examples 9 to 14, comprising means for passing from a paired stimulation to a coupled stimulation, in other words to an entirely stimulated rhythm, said means being sensitive to the electrocardiogram and/or hemodynamics and/or myocardial metabolism acquisition means.

16. Device according to any one of examples 1 to 15, for treating isolated premature arrhythmias and extrasystoles, comprising a plurality of electrodes disposed at different locations of the heart muscle and acquisition means which are sensitive to the electrical signals appearing at the electrodes or remotely for observing, at an early stage, the occurrence of an electrical extrasystole in a myocardial zone close to that of the electrodes initially concerned, the stimulating pulse sending means thus being made sensitive to such an observation so as to emit, in a nearby electrode or in a plurality of electrodes, a stimulating pulse or burst of which the electrical propagation into the myocardium is directed toward the myocardial zone affected by the extrasystole and causing fusion between the spontaneous and stimulated depolarizations which blocks the propagation of the extrasystole.

17. Device according to any one of examples 1 to 15 for treating isolated arrhythmia and extrasystoles, comprising one or more electrodes, in particular juxta- or extracardial or intracavitary ventricular electrodes, in particular without exclusive contact with the myocardium, for the instantaneous detection of a premature extrasystole, said device being arranged so as to instantaneously trigger, if said extrasystole is detected, the stimulation by a pulse or by a burst of pulses from all the available stimulating electrodes, thus creating a fusion complex between the propagations of the stimulated and extrasystolic depolarizations.

18. Device according to any one of examples 1 to 17, comprising means for rapidly detecting an extrasystole, the means of the device being sensitive to the acquisition of this extrasystole for reducing or even eliminating, preferably temporarily, the electrical diastolic phases (D), in particular either by increasing the stimulation rhythm in the heart with electrical control of the device or by taking the control to send a stimulating pulse at the very beginning of the electrical diastole.

19. Device according to any one of examples 1 to 18 comprising means for increasing, should an arrhythmia corresponding to predetermined criteria occur, the number and/or intensity of the pulses of the burst to potentiate the effect of stabilization on the myocardial cell membranes.

20. Device according to any one of examples 1 to 19, comprising means for reducing, in the event of arrhythmia, the intensity of the pulses of the burst, the device thus monitoring whether arrhythmia continues.

21. Device according to any one of examples 1 to 20, arranged so as to acquire a cardiac mechanogram, in particular until the occurrence of a cycle which is sufficiently long to obtain a good myocardial contraction, the stimulating means being arranged so as to transmit a stimulating pulse or burst only at the peak of the mechanical contraction (MMRZ) located within the plateau of the mechanogram curve, in particular just before the end of the electrical refractory zone (ERZ), after which the device stimulates, immediately after the end of the electrical refractory zone which has just been extended, thus canceling the electrical diastole.

22. Device for stimulating and/or potentiating the heart muscle and/or the myocardial cells, for significantly increasing the hemodynamic performance of the heart and/or the treatment of auricular tachycardia, tachyarrhythmia or fibrillation comprising:
  means for the precise acquisition of the cardiac hemodynamics (5, 6) and comprising a means for instantaneous detection of the maximum myocardial refractory zone (MMRZ) at a precise location of the myocardium,
  and means for sending at least one stimulating pulse and preferably a burst of stimulating pulses from the local region in which the occurrence of the zone MMRZ is detected.

23. Device according to example 22 comprising means for automatic acquisition (1, 2, 3) of the heart rhythm and optionally of its origin, in particular for obtaining the interval between at least the last two waves R (induced or spontaneous) of the cardiac cycle which has just been completed and means (4) for determining continually in real time the duration of the electrical refractory period (ERZ) following the last wave R of a cardiac cycle, said device being arranged so as to detect whether an electrical depolarization signal has been produced by said stimulation in said zone MMRZ.

24. Device according to any one of examples 22 and 23, comprising means for detecting and storing the duration of said maximum myocardial refractory zone (MMRZ) and sending said local stimulating pulse or burst of stimulating pulses after a short duration after the beginning, in the current cycle, of the beginning of said zone MMRZ and before the estimated end of said zone by storing said duration in the preceding cycles.

25. Device according to any one of examples 2 to 24 wherein the stimulating pulse or at least one stimulating pulse of a burst falls in said zone (MMRZ), substantially at the location of the myocardium where the occurrence of said zone (MMRZ) is detected.

26. Device according to any one of examples 1 to 25 comprising implanted means for measuring intracavitary pressure and capable of detecting a zone of maximum pressure in the plateau of the cardiac mechanogram and to which said means for transmitting a stimulating pulse or burst are sensitive.

27. Device according to any one of examples 1 to 25 comprising at least one sensor for detecting intramyocardial pressure.

28. Device according to example 27, wherein said intramyocardial pressure sensor is located in the intra-auricular septum and/or in a free cardiac or intraventricular wall.

29. Device according to any one of examples 1 to 25 comprising means for measuring the variation in the volume of the heart or a portion of the heart, detecting and storing the interval of the cycle where said volume has reached and maintained its minimum value, said means for sending a stimulating pulse or burst being sensitive to said measuring means.

30. Device according to any one of examples 2 to 29 comprising means for detecting the oxygen consumption of the heart and/or an equivalent, in particular the local pH or concentration of ketone bodies and means for detecting the zone of maximum cardiac contraction (MMRZ) by estimation by detecting, during one or more previous cycles, the relative position in the cycle and/or in the mechanogram of the pulse or the pulse of a burst which has generated a post-extrasystolic potentiation (PESP) with minimal oxygen consumption relative to the measured blood flow per minute.

31. Device according to any one of examples 2 to 30 comprising
    means for continuously measuring electrical refractory zones ERZ in a location of the heart,
    means disposed substantially in the heart region for precisely measuring the zones of maximum myocardial contraction MMRZ,
    the device being arranged so as to acquire, from said means, the temporal superimposition, in the same cycle, of said zones ERZ and MMRZ and determine the common zone known as the critical zone ECZ.

32. Device according to example 31, wherein means are arranged so as to immediately send at least one stimulating pulse into said region of the heart, during said zone ECZ.

33. Device according to example 32, wherein said means for checking the temporal superimposition are sensitive to a shift between the zones ERZ and MMRZ in order to send a stimulating pulse or burst supplying at least one pulse to the interior of the zone ECZ.

34. Device according to example 33 wherein said sensitive means allow the time interval between two pulses of a burst to be reduced so as to increase the probability of having a pulse during said zone ECZ.

35. Device according to example 34, wherein the duration between two pulses of a burst cannot be reduced to less than a value of approximately 10 ms.

36. Device according to any one of examples 31 to 35 wherein, if it is impossible to cause at least one pulse to travel to the interior of the zone ECZ, the device stops the coupled or paired stimulation.

37. Device according to any one of examples 2 to 36, wherein the occurrences and time durations of the zones ECZ are stored during a plurality of cycles and the development thereof is analyzed in order to anticipate any tendency to the suppression of said zone ECZ and, in this case, to implement a treatment, in particular by perfusion of drugs or change of the OIST rhythm in order to act on the duration of the zones ERZ or MMRZ or the overlap thereof.

38. Device according to any one of examples 1 to 37 comprising:
    means for acquiring information relating to a patient's electrocardiogram, including the heart rhythm,
    means for acquiring information relating to the patient's hemodynamic performance,
    analysis means which are sensitive to said acquisition means for stimulating the effect of inotropic paired or coupled stimulation adapted to the patient's heart.

39. Device according to example 38, further comprising means for automatically comparing said acquired information relating to the patient's hemodynamic performance with the simulated effect on said performance of an inotropic paired stimulation.

40. Device according to any one of examples 38 and 39, wherein said acquisition and comparison means allow the acquisition and comparison of the information cycle by cycle.

41. Device according to any one of examples 38 to 40, wherein said means for collecting information relating to the patient's hemodynamic performance measure at least one of the following parameters relating to the cardiac contraction:
    gradient (dp/dt) of the phases of ascent and/or descent of the intracavitary and/or intramyocardial pressure;
    duration of the systolic pressure plateau, corresponding to systolic ejection;
    duration of the systole (cardiac contraction);
    duration of the diastole (fast and slow active motor filling phases);
    ratio of diastole and systole durations;
    quality of the diastole, in particular filling depression;
    electromechanical coupling (period separating the beginning of a QRS complex from the beginning of the mechanical systole which it causes);
    shift between the intramyocardial contraction curve close to the local detecting electrode and the global intracavitary contraction curve.

42. Device according to any one of examples 38 to 41, comprising means for comparing information relating to the electrocardiogram and to the hemodynamic performance of a simulation of inotropic paired or coupled stimulation with corresponding information acquired during a subsequent identical or similar actual inotropic stimulation.

43. Device according to any one of examples 38 to 42, comprising means for acquiring or calculating a threshold level of values of the information on the simulated hemodynamic performance adapted to the patient and, if the threshold is exceeded, causing an identical or similar inotropic paired or coupled actual stimulation.

44. Device according to any one of examples 38 to 43, wherein said means for acquiring the information relating to the patient's electrocardiogram and to the patient's hemodynamic performance are arranged so as to acquire this information at different rhythms.

45. Device according to example 44, arranged so as to temporarily impose, on the patient's heart, rhythms which vary in increments or progressively and during which said information relating to the electrocardiogram and said information relating to the corresponding hemodynamic performance are acquired.

46. Device according to any one of examples 38 to 45, wherein said means sensitive to the acquisition means are arranged so as to simulate the effect of a plurality of inotropic paired or coupled stimulations at different heart rhythms.
47. Device according to any one of examples 38 to 46, arranged so as to carry out said comparison during a limited number of cycles of the actual inotropic stimulation and, if the absence of a satisfactory level of hemodynamic performance is observed, to terminate the current stimulation.
48. Device according to example 47 wherein said number of cycles is approximately 10 or less, in particular 1, 2 or 3 cycles.
49. Device according to any one of examples 47 and 48, arranged so as, if an adequate increase in initial hemodynamic performance is observed, to continue the inotropic stimulation and to detect and store whether the increase in initial hemodynamic performance is maintained and/or further increases progressively for a greater number of cycles.
50. Device according to example 49, wherein said greater number of cycles is at least about 100 cycles.
51. Device according to any one examples 38 to 50, wherein said analysis means are arranged so as to include the medicinal inotropic effects likely to interfere with the effect of electrical inotropic stimulation.
52. Device according to any one of examples 38 to 51, comprising means for emphasizing, visually and/or quantitatively by calculation, the differences between the curves for the simulation and for the corresponding actual stimulation.
53. Use of a device according to any one of examples 1 to 52 for the production of a device for treating acute or severe heart failure.
54. Use of a device according to any one of examples 1 to 52 for preparing an assembly intended for carrying out a process for cardiac regeneration comprising the following steps:
    implanting in the heart, in particular in a right or left atrium and/or a right or left ventricle, regeneration cells, in particular in the sub-endocardial or intramyocardial position, in particular in a plurality of encapsulated groups of cells or in a cell blanket or cell mesh,
    and carrying out stimulation according to the invention, preferably paired stimulation.
55. Process for stimulating the heart muscle to allow a significant increase in hemodynamic performance of the heart and/or the treatment of tachycardia comprising the following steps:
    providing a permanently implanted heart stimulation device and, with the aid of this device,
    automatically acquiring the heart rhythm so as to obtain, in particular, the interval between at least the last two waves R (induced or spontaneous) of the just completed cardiac cycle,
    determining in real time, in particular on request, preferably continually, the duration of the electrical refractory period (ERZ) following the last wave R of said cycle,
    and sending at least one stimulating pulse substantially without delay at the end of said refractory period (ERZ).
56. Process according to example 55, wherein there are used means (4) for determining the duration of the electrical refractory period (ERZ), which are sensitive to the detection of that pulse in a burst which has triggered a complex R', and means for determining the maximum mechanical refractory zone MMRZ, and a zone ECZ posterior to the electrical refractory zone ECZ is determined in said zone MMRZ and, if said zone ECZ exists, at least one stimulating pulse is sent into said zone ECZ.
57. Process according to either example 55 or example 56, even when the device generates a single stimulating pulse instead of a burst, wherein the substantially exact duration of the refractory zone is acquired, for example by scanning of a second pulse, this scanning being carried out, for example, during the preceding cardiac cycles or the current cycle.
58. Process according to either example 55 or example 56, wherein the beginning of the burst of stimulating pulses is selected so as to begin just before the estimated end of the refractory period, and the duration of this burst and consequently the number of stimulating pulses is advantageously such that at least one stimulating pulse will occur before and a following pulse very quickly after the end of said refractory period.
59. Process according to any one of examples 55 to 58, wherein there are used means for advancing or retarding the occurrence of the burst relative to an estimation of the refractory zone and/or modifying the pulse interval within the burst, the device having automatic acquisition means, in particular by obtaining the intracardiac ECG for determining, in particular by processing the intracardiac electrical signal in the region of the detecting and/or stimulating electrode, which stimulating pulse in the burst triggered the wave R', and thus obtaining the electrical refractory zone (ERZ) and functionally modifying the burst.
60. Process according to any one of examples 55 to 59, wherein there are used means which are sensitive the spontaneous or stimulated waves R and/or to the determination of the electrical and/or mechanical refractory zones, in particular by scanning all of the burst or only within this burst and/or means for the instantaneous determination of the heart excitability thresholds, for example by providing stimulating pulses of variable intensity, including subliminal pulses for allowing the measurement thereof within the burst.
61. Process according to any one of examples 55 to 60, wherein there are used anti-tachycardic stimulation means and extrasystole-sensitive means for automatically stopping said stimulation on the occurrence of excessive hemodynamic instability and electrical arrhythmia corresponding to preselected criteria.
62. Process according to any one of examples 55 to 61, wherein precisely measured cardiac hemodynamic (5, 6) information is further acquired.
63. Process according to example 62, wherein there are used one or more intracardiac pressure sensors or such sensors disposed in the proximity of the heart and sensors for determining variations in heart volume, for example electrical impedance or echographic sensors.
64. Process according to either example 62 or example 63, wherein, in addition to the rhythm acquisition means, means for determining the duration of refractory zone and means for transmitting a pulse or a burst, there are used means (7, 10) which are sensitive to the precise acquisition of the hemodynamics for determining the variations in efficacy of the hemodynamics, these means being capable of controlling the transmission and optionally the parameters of the pulse or the burst, preferably in a manner resembling that which produced the hemodynamics which are most favorable for the patient at a given moment.
65. Process according to example 64, wherein said means act on parameters such as: a programmed ventricular rhythm and/or an automatic adjustment of the beginning or end or duration of the burst or the number or the characteristics, in particular width, intensity, polarity, density, interval of the pulses in the burst, or else a location of the transmission of the burst at one or more stimulating electrodes.

66. Process according to any one of examples 55 to 65, wherein there are used means for progressively reducing a burst to a single pulse, in particular by probing periodically with at least a second pulse which travels progressively ahead of the stimulating pulse so as to automatically measure the beginning of the non-refractory zone in such a way that, when the exploratory pulse retracts toward he stimulating pulse, this pulse itself can be retracted, in particular periodically in the event of operational instability, until the beginning of reduction of the precise ventricular pressure/volume curve or increase in the oxygen consumption or in blood acidosis (pH) or in myocardial membrane secretion of electrons, this position being able to correspond to the exceeding of the end of the mechanical refractory zone with maximum active contraction (MMRZ).

67. Process according to any one of examples 55 to 66, wherein there are acquired metabolic parameters, in particular of oxygen consumption and/or equivalents thereof such as the measurement of electron densities of myocardial cell membrane or increase in ketone bodies, lactic acid, etc.

68. Process according to any one of examples 55 to 67, wherein there are used means for passing from paired stimulation to coupled stimulation, said means being sensitive to the means for acquiring the electrocardiogram and/or the hemodynamics and/or the myocardial metabolism.

69. Process according to any one of examples 55 to 68, for treating isolated arrhythmia and extrasystoles, wherein a plurality of electrodes disposed at different locations of the heart muscle are implanted and, with acquisition means which are sensitive to the electrical signals appearing at the electrodes, the local occurrence of an electrical extrasystole in a myocardial zone is observed at an early stage, the stimulating pulse transmission means thus being made sensitive to such an observation so as to instantaneously emit in a nearby electrode or in a plurality of electrodes, a stimulating pulse or burst of which the electrical propagation into the myocardium is directed toward the myocardial zone affected by the extrasystole so as to lead to a fusion complex between the stimulated and extrasystolic depolarization which blocks the propagation of the extrasystole.

70. Process according to any one of examples 55 to 69 wherein, if an extrasystole is detected quickly, the electrical diastolic phases (D) are reduced or eliminated, preferably temporarily, in particular either by increasing the stimulation rhythm in a heart with electrical control of the device or by taking the control so as to send a stimulating pulse at the very beginning of the electrical diastole.

71. Process according to any one of examples 55 to 70 wherein, if an arrhythmia corresponding to preselected criteria occurs, the number and/or intensity of the pulses of the burst are increased to potentiate the effect of stabilization of the myocardial cell membranes, subject to the simultaneous observation of maintenance of electrical and hemodynamic tolerance.

72. Process according to any one of examples 55 to 71, wherein there are used means for . . . and reducing, in the event of arrhythmia corresponding to preselected criteria, the intensity of the pulses of the burst, the device thus monitoring whether the arrhythmia continues or improves.

73. Process for inotropic cardiac stimulation according to any one of examples 55 to 72, characterized by the following steps:

the electrical heart signals, including premature extrasystoles, are detected at an extracardiac, preferably epicardial or thoracic or intracavitary level, by means of a plurality of detection electrodes implanted in various parts of the heart or in the vicinity thereof, it is determined whether a given extrasystole is dangerous, for example by being premature or of ventricular origin, and a stimulating train is instantaneously transmitted in the region of at least one stimulating electrode.

74. Process according to any one of example 73 wherein the device comprises stimulating electrodes in various intra- or juxta-cardiac locations and stimulation is simultaneously carried out from a plurality or all of these electrodes to induce the fused QRS complexes blocking the still non-refractory myocardial spaces before the arrival of detected extrasystole propagation.

75. Process according to either example 73 or example 74, wherein sequential recording and storing of the extrasystoles, in particular the extrasystoles which are considered to be dangerous, is carried out and, in the event of repetition, preventive stimulation, in particular by temporary acceleration of a stimulation base rhythm is carried out.

76. Process according to any one of examples 55 to 75, wherein continuous monitoring of the excitability thresholds of the heart muscle comprising the following steps is carried out:

inotropic stimulation is carried out by transmitting a pulse train in such a way that a pulse of the train occurs very shortly after the end of the refractory period of the heart, the stimulation-inducing pulse of the pulse train is identified, during the following cardiac cycles, the energy of the stimulating pulse thus detected is reduced progressively or abruptly to the level where said pulse of the train becomes ineffective and therefore subliminal, the following pulse of the train thus causing stimulation, and the energy of the subliminal pulse is recorded and thus determines an excitability threshold zone.

77. Process according to example 76, characterized by the following steps:

it is checked that the threshold or the excitability threshold zone remains substantially stable, and the energy of the pulses in the burst is reduced to a value which is lower, but higher than the excitability threshold, while simultaneously checking the regular continuation of the stimulated electrical complexes.

78. Process according to either example 76 or example 77 wherein the energy amplitude of the first pulses of a burst is reduced to a level lower than the excitability threshold, it is observed whether or not this subliminal stimulation-inducing reduction reduces the myocardial excitability threshold, and, if this threshold is reduced, the intensity of the following pulses of the burst is reduced while simultaneously checking the regular continuation of the stimulated complexes.

79. Process according to example 78, comprising the following steps:

the energy amplitude at which the stimulating pulse or the stimulating train or a portion of the train will become subliminal and will no longer generate observable stimulation is detected, then the energy amplitude of the pulse which has become subliminal or the portion of the pulse train which has become subliminal is increased instantaneously during the next cardiac cycles.

80. Process according to example 79, wherein the energy amplitude of the pulses is progressively increased in order to determine the new myocardial excitability threshold relative to the geometric shape and the location of the electrodes.

81. Process according to any one of examples 55 to 80, wherein a stimulating pulse or burst is sent inside the zone MMRZ situated inside the plateau of the contraction curve of the mechanogram and during which the contraction of the myocardium is substantially at its peak.

82. Process according to example 81, wherein the pulse or at least one pulse of a stimulation burst falls within said zone MMRZ.

83. Process according to any one of examples 81 and 82, wherein said zone MMRZ is acquired automatically.

84. Process according to example 83, wherein the infra-cavitary pressure is measured by a sensor and a zone of maximum pressure is selected in the systolic plateau of the cardiac mechanogram in which the transmission of a stimulating pulse or burst is induced.

85. Process according the example 83, wherein the local intramyocardial pressure is measured in the vicinity of a detecting and stimulating electrode.

86. Process according to example 85, wherein the myocardial pressure is detected in the intra-auricular and/or intraventricular septum.

87. Process according to example 83, wherein the variation in the volume of the heart or a part of the heart is measured by detecting the zone where said volume has reached and maintains its minimum value.

88. Process according to any one of examples 81 to 87, wherein the oxygen consumption of the heart is measured and the zone of maximum cardiac contraction (MMRZ) is detected by estimation by detecting, during one or more previous cycles, the relative position, in the cycle and/or in the mechanogram, of the pulse or the pulse of a burst which has generated post-extrasystolic potentiation (PESP) without a significant increase in energy consumption.

89. Process according to any one of examples 55 to 88, wherein:
information to relating to a patient's electrocardiogram, including the heart rhythm, is acquired,
information relating to the patient's hemodynamic performance is acquired;
and this information is used to simulate the effect of prolonged inotropic paired or coupled stimulation.

90. Process according to example 89 wherein said acquired information relating to the patient's hemodynamic performance is additionally compared to the simulated effect on said performance of an inotropic paired stimulation.

91. Process according to either example 89 or example 90, wherein the information is acquired and compared cycle by cycle.

92. Process according to any one of examples 89 to 91, wherein at least one of the following parameters relating to cardiac contraction is measured:
gradient (dp/dt) of the phases of ascent and/or descent of the intracavitary and/or intramyocardial pressure;
duration of the systolic pressure plateau, corresponding to systolic ejection;
duration of the systole (cardiac contraction);
duration of the diastole (filling phase);
ratio between diastole and systole durations;
quality of the diastole, in particular filling depression or speed and amplitude of the fast and slow phases;
electromechanical coupling (period separating the beginning of a QRS complex from the beginning of the mechanical systole which it causes);
shift between the local intramyocardial contraction curve and the global ventricular intracavitary contraction curve.

93. Process according to any one of examples 89 to 92, wherein information relating to the electrocardiogram and to the hemodynamic performance of a simulation of inotropic paired or coupled stimulation is compared with corresponding information acquired during a subsequent identical or similar actual inotropic stimulation.

94. Process according to any one of examples 89 to 93, wherein a threshold level of values of information on the simulated hemodynamic performance of the patient is acquired or calculated and, if the threshold is exceeded, an identical or similar inotropic paired or coupled actual stimulation is triggered.

95. Process according to any one of examples 89 to 94, wherein the information relating to the patient's electrocardiogram and to the patient's hemodynamic performance is acquired at different rhythms, in particular rhythms which increase or decrease by increments or progressively.

96. Process according to any one of examples 89 to 95, wherein there are used means which are sensitive to said acquisition means arranged so as to simulate the effects of a plurality of inotropic paired or coupled stimulations at different heart rhythms.

97. Process according to any one of examples 89 to 96, wherein said comparison is effected for a limited number of cycles of the actual inotropic stimulation and, if the absence of a satisfactory hemodynamic performance level is observed, the current inotropic stimulation is terminated.

98. Process according to example 97, wherein said number of cycles is approximately 10 or less, in particular 1, 2 or 3 cycles.

99. Process according to either example 97 or example 98 wherein, if an adequate initial increase in hemodynamic performance is observed, inotropic stimulation is continued and it is detected whether the initial increase in hemodynamic performance is maintained and/or still increases progressively for a greater number of cycles.

100. Process according to example 99, wherein said greater number of cycles is at least about 100 cycles.

101. Process according to any one of examples 89 to 100, wherein the effects of cardiovascular target medicaments, which have previously been administered or are being administered, are used in the analysis.

102. Process according to any one of examples 89 to 101, wherein the differences between the simulation and stimulation curves are emphasized visually and/or quantitatively, in particular by superimposition of the curves.

103. Process according to any one of examples 55 to 102, wherein the cardiac mechanogram is acquired, in particular until the appearance of a cycle which is long enough to obtain a good myocardial contraction, and a stimulating pulse or burst is then transmitted at an instant within the plateau of the mechanogram curve (MMRZ), in particular just before the end of the electrical refractory zone (ERZ), and stimulation is then carried out immediately after the end of the electrical refractory zone which will cause a new electrical refractory zone.

104. Process according to any one of examples 55 to 103, wherein there is defined a first threshold of increase in global hemodynamic performance/min and/or per cardiac contraction, in particular the cardiac output, said threshold being equal to at least 15% or preferably 25% of the performance prior to treatment, and the stimulation parameters are adjusted until at least said threshold value is obtained.

105. Process according to example 104, wherein, if the increase according to said first threshold value is not obtained during a period of approximately 1 to 10 contractions, the treatment is stopped.

106. Process for treating acute or severe heart failure wherein:
the heart rhythm and, in particular, the interval between at least the last two waves R (induced or spontaneous) of a cardiac cycle which has just been completed are automatically acquired,
the duration of the electrical refractory period (ERZ) following the last wave R of said cycle is determined, preferably continually,
at least one stimulating pulse and preferably a stimulating pulse burst is sent substantially without delay at the end of the refractory period (ERZ), the duration of the burst being such that, in view of the pulse repetition interval in the burst, a stimulating pulse of the burst is sent to the heart substantially without delay after the end of the refractory period, and
these steps are repeated for a series of at least three contractions if an initial improvement in cardiac performance is observed,
and, in the absence of an improvement, the process is automatically stopped.

107. Process according to example 106, wherein the total mechanical performance of the heart, in particular its blood flow and/or the variation in ventricular volume is compared, on the one hand, before carrying out the steps of the process and, on the other hand, after carrying out the steps of the process and, if the increase in heart performance is greater than 15%, the steps of the process are carried out again.

108. Process for cardiac resuscitation in a patient suffering from severe or critical heart failure wherein:
the heart rhythm and, in particular, the interval between at least the last two waves R (induced or spontaneous) of a cardiac cycle which has just been completed is automatically acquired,
the duration of the electrical refractory period (ERZ) following the last wave R of said cycle is determined, preferably continually,
at least one stimulating pulse and preferably a stimulating pulse burst is sent substantially without delay at the end of the refractory period (ERZ), the duration of the burst being such that, in view of the pulse repetition interval in the burst, a stimulating pulse of the burst is sent to the heart substantially without delay after the end of the refractory period, and
these steps are repeated for a series of at least three contractions if an initial improvement in cardiac performance is observed, and
these steps are repeated at least until an at least progressive improvement in detectable cardiac performance is achieved.

109. Process according to any one of examples 106 to 108, also comprising the steps of the process according to example 56.

110. Process for in vitro stimulation of cells intended to be implanted in the heart, said process comprising the following steps:
obtaining and cultivating, in vitro, regeneration cells, preferably in the form of small groups or confluent cultures, so as to be in mutual contact;
placing the confluent cells in electrically conductive contact with one another and optionally with the cells of a previously taken myocardial tissue and with an electrical stimulation device,
periodically sending electrical pulses to said cultivated cells;
detecting the electrical depolarization responses of the cells and/or membrane potentials, and/or electrical refractory zones.

111. Process according to example 110 wherein the stimulation is a simple electrical stimulation at a rhythm preferably approximating a normal heart rhythm, followed after an initial period by a paired or coupled stimulation according to any one of examples 1 to 20, once the groups of cells in culture are synchronized so as to manifest an electrical refractory period, in particular a period relatively close to that of the cells of the heart intended to receive the cells.

112. Process according to any one of examples 110 and 111, wherein the cells have been modified so as to over-express telomerase or Sir2 protein.

113. Process for preparing living cells, in particular vegetable, animal and human cells, which can be reimplanted prophylactically or therapeutically, wherein a nucleus of a dedifferentiated cell is transported in an oocyte, preferably an unfertilized or recently fertilized oocyte from a homologous or heterologous mammal, previously preferably completely or partially freed of its nucleus, so as to induce a stage of mitosis of the transferred nucleus, in that this nucleus is removed during the mitosis and before the end of it, then this nucleus which is partially dedifferentiated in mitosis at this stage is introduced into a cell, preferably after some part or the totality of its nucleus or nuclei have been removed from it, so as to induce and terminate the differentiating nuclear division thereof and to form a cell strain or a tissue at a less advanced stage of differentiation than said differentiated cell.

114. Process according to any one of examples 110 to 113 wherein the transferred nucleus is extracted at the metaphase stage of the first mitosis.

115. Process according to any one of examples 110 to 113, wherein the transferred nucleus is extracted at the anaphase stage of the first mitosis.

116. Process according to any one of examples 110 to 113, wherein the transferred nucleus is removed at the prophase stage of the first mitosis.

117. Process according to any one of examples 110 to 113, wherein the transferred nucleus is removed at the telophase stage of the first mitosis.

118. Process according to any one of examples 110 to 117, wherein a nucleus of myocardial, muscle or auto-rhythmic cardiac cell, in particular sinusal cells from the Tawara's node or fibers from the His' bundle or Purkinje bundle are transferred into the oocyte.

119. Process according to example 118, wherein the removed nucleus is introduced, before the end of its intra-oocyte mitosis, into a myocardial or muscle cell, which is preferably freed of its nucleus or some or all of its nuclei.

120. Process according to either example 118 or example 119, wherein the partially dedifferentiated cells obtained are subjected, preferably after or during the cell multiplication culture thereof after the formation of a confluent assembly, to periodic electrical stimulation of the cardiac stimulation type, in particular according to any one of examples 22 to 24.

121. Process according to example 120, wherein said cells are subjected to coupled or paired electrical stimulation in which this pulse without a contractile effect is sent just after the end of the electrical refractory period of the cells in culture.

122. Process according to example 120, wherein said cells are subjected to electrical stimulation in cycles comprising a first stimulating pulse and, toward the end of the refractory period, a pulse train, so that at least one of the pulses of the train falls just after the end of the electrical refractory period of the cells and during their mechanical refractory zone of maximum contraction.

123. Process according to any one of examples 55 to 109 wherein, before carrying out the steps of the process, myocardial or muscle or similar cells, in particular cells obtained by a process according to any one of examples 100 to 112, are implanted in the heart.

124. Process wherein the cells obtained by the process according to any one of examples 110 to 123 are implanted in the region of the auricular myocardium, in particular in the case of a patient suffering from auricular fibrillation.

125. Process according to any one of examples 113 to 117 wherein nuclei or parts thereof of cells of pilose follicles and/or melanocytes allowing regeneration of hair and/or the coloring thereof are transferred into the oocyte.

126. Arterial segment or stent, in particular with a coronary, aortic, carotid, renal or femoral target, comprising a structure which is coated or colonized by cells obtained by the process according to any one of examples 110 to 122.

127. Physiological arterial segment or stent consisting of living, auto-contractile and elastic, in particular autologous, cells, cultivated according to any one of examples 110 to 122.

128. Arterial segment or stent according to either example 126 or example 127 shaped in the manner of an arterial stent arranged so as to be introduced into an arterial lumen.

129. Segment or stent according to examples 126 to 128, comprising means for electrical stimulation of the arterial type, coordinated with the ventricular diastole, of said cells of the segment.

130. Segment or stent according to any one of examples 126 to 129, comprising at least one stimulating and/or detecting electrode.

131. Segment or stent according to example 130, wherein the stimulating and/or detecting electrode has been introduced into the cell culture so as to be surrounded by said living cells.

132. Segment or stent according to any one of examples 126 to 131 comprising a sensor, in particular for measuring oxygen saturation and/or metabolic parameters and a detecting or stimulating electrocardiographic sensor.

133. Segment or stent according to any one of examples 126 to 132, comprising a plurality of electrodes arranged so as to obtain the variations in local electrical impedance.

134. Arterial segment or stent according to any one of examples 126 to 133 having a structure, in particular in expansible meshes supporting different cell layers, such as an endoartery, myoartery and periartery structure, said structure allowing a spontaneous increase with progressive widening of its lumen and creation of vascularization which nourishes, in particular, the myoarterial portion.

135. Segment according to any one of examples 126 to 134, wherein the structure is produced from at least one of the following materials: PLGA, collagen, globin.

136. Arterial stent without living cells having a structure which is radially expansible but sufficiently rigid to keep the arterial aperture open at least in systole, which is optionally biodegradable or removable by a catheter and capable of receiving a physiological stent according to any one of examples 126 to 135.

137. Tissue block for implantation in or on the heart and comprising a segment according to any one of examples 127 to 135, surrounded by its functional block of peripheral vasculo-myocardial tissue provided with arteries, arterioles, and capillary and venous network, which can be sewn or anchored in or on the recipient's myocardium.

138. Biological cardiac pacemaker comprising partially dedifferentiated cardiac auto-rhythmic cells or tissues according to any one of examples 110 to 122, which is preferably autologous or homologous, originates from the recipient's organism and is intended to be implanted in the heart or in a defective region of the heart.

The invention claimed is:

1. A method carried out by a device for stimulating and/or potentiating heart muscle and/or myocardial cells, comprising:
   detecting an interval between at least the last two R waves of a cardiac cycle just completed;
   detecting a mechanical refractory zone of maximum myocardial contraction (MMRZ);
   determining, in real time, the duration of the electrical refractory period (ERZ) following the last R wave of said cycle;
   determining the position and duration of an effective critical zone (ECZ), which is placed immediately after the end of the ERZ and terminates at the end of a refractory zone of maximum myocardial contraction MMRZ; and
   sending, substantially without delay at the end of said refractory period (ERZ), at least one of a paired stimulating pulse and a coupled stimulating pulse adapted to said functional cell state, the transmission of said stimulating pulse intervening in said ECZ zone.

2. A method according to claim 1, wherein detecting a mechanical refractory zone of maximum myocardial contraction (MMRZ) comprises periodically detecting the excitability threshold of the myocardium during one or each cardiac cycle.

3. A method according to claim 1, wherein sending the at least one of the paired stimulating pulse and the coupled stimulating pulse comprises sending a burst of stimulating pulses substantially at the end of said refractory period (ERZ), wherein the duration of the burst and the pulse repetition interval apply a stimulating pulse of the burst to the heart substantially without delay after the end of said refractory period.

4. A method according to claim 3, wherein determining the duration of the electrical refractory period (ERZ) comprises determining which pulse of the burst triggered a complex (R').

5. A method according to claim 1, wherein sending the at least one of the paired stimulating pulse and the coupled stimulating pulse comprises sending a single stimulating pulse instead of a burst, and wherein determining the duration of the refractory zone comprises acquiring, by scanning a second pulse, the substantially exact duration of the refractory zone, this scanning being carried out during one of a plurality of preceding and current cardiac cycles.

6. A method according to claim 1, further comprising determining whether the ECZ is of a duration sufficient for sending the at least one of the paired stimulating pulse and the coupled stimulating pulse entirely within the ECZ, and sending the at least one of the paired stimulating pulse and the coupled stimulating pulse within the ECZ if the ECZ is determined to be of sufficient position and duration.

7. A method carried out by a device for stimulating and/or potentiating heart muscle and/or myocardial cells, comprising:

detecting the maximum myocardial refractory zone (MMRZ) at a precise location of the myocardium; and sending, during the MMRZ, at least one stimulating pulse from the local region in which the occurrence of the zone MMRZ is detected.

* * * * *